(12) United States Patent
Kuramoto et al.

(10) Patent No.: US 8,957,212 B2
(45) Date of Patent: Feb. 17, 2015

(54) PHOTOBASE GENERATOR

(75) Inventors: Ayako Kuramoto, Kawagoe (JP);
Motoshige Sumino, Kawagoe (JP);
Nobuhiko Sakai, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 325 days.

(21) Appl. No.: 13/132,216

(22) PCT Filed: Dec. 1, 2009

(86) PCT No.: PCT/JP2009/070179
§ 371 (c)(1),
(2), (4) Date: Jun. 1, 2011

(87) PCT Pub. No.: WO2010/064631
PCT Pub. Date: Jun. 10, 2010

(65) Prior Publication Data
US 2011/0233048 A1 Sep. 29, 2011

(30) Foreign Application Priority Data

Dec. 2, 2008 (JP) ................................. 2008-306919
Apr. 14, 2009 (JP) ................................. 2009-097824

(51) Int. Cl.
*C07D 295/205* (2006.01)
*C07C 271/24* (2006.01)
(Continued)

(52) U.S. Cl.
CPC ............ *C07D 211/44* (2013.01); *C07C 271/12* (2013.01); *C07C 271/24* (2013.01);
(Continued)

(58) Field of Classification Search
USPC ..................................... 204/157.82; 546/245
See application file for complete search history.

(56) References Cited

U.S. PATENT DOCUMENTS 6,057,380 A   5/2000  Birbaum et al.
6,531,506 B1  3/2003  Kroetz et al.
(Continued)

FOREIGN PATENT DOCUMENTS

JP       10-77264     3/1998
JP       11-71450     3/1999
(Continued)

OTHER PUBLICATIONS

Yamato; J. Chem. Soc., Perkin Trans. 1, 1997, 1193-1199.*
(Continued)

*Primary Examiner* — John Mabry
*Assistant Examiner* — Daniel Carcanague
(74) *Attorney, Agent, or Firm* — Hamre, Schumann, Mueller & Larson, P.C.

(57) ABSTRACT

There is intended to provide the novel compounds which generate a base easily when irradiated with long wavelength light (active energy rays), a photobase generator containing the compounds and a photobase generation method, and the present invention relates to the compounds represented by the general formula [1], a photobase generator containing the compounds and a photobase generation method:

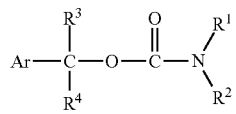

[1]

(wherein, Ar represents any of groups with specific structures selected from the group consisting of an anthracenyl group, an anthraquinonyl group and a pyrenyl group; $R^1$ and $R^2$ each independently represent a hydrogen atom or a linear, branched or cyclic alkyl group having 1 to 10 carbon atoms, or represent ones which can form an alicyclic ring containing nitrogen atom(s) or an aromatic ring containing nitrogen atom(s) together with a nitrogen atom to which they are bound, which the rings having 3 to 8 carbon atoms which may have a substituent, $R^3$ and $R^4$ each independently represent a hydrogen atom, a linear, branched or acyclic alkyl group having 1 to 10 carbon atoms).

28 Claims, 6 Drawing Sheets

(51) Int. Cl.
*C07C 271/12* (2006.01)
*C07C 50/18* (2006.01)
*C07D 233/60* (2006.01)
*C07D 295/192* (2006.01)
*C07D 211/46* (2006.01)
*B01J 19/08* (2006.01)
*C07D 211/44* (2006.01)
*C07D 295/20* (2006.01)

(52) U.S. Cl.
CPC ............ *C07D211/46* (2013.01); *C07D 233/60* (2013.01); *C07D 295/20* (2013.01); *C07D 295/205* (2013.01); *C07C 2101/14* (2013.01); *C07C 2103/24* (2013.01)
USPC ...... 546/245; 546/203; 546/195; 204/157.82; 548/334.5; 560/1; 560/163; 552/266

(56) References Cited

U.S. PATENT DOCUMENTS

| | | | |
|---|---|---|---|
| 6,656,737 | B1 | 12/2003 | Streicher |
| 2003/0215801 | A1 | 11/2003 | Pieken et al. |
| 2005/0181300 | A1 | 8/2005 | Okazaki et al. |

FOREIGN PATENT DOCUMENTS

| | | |
|---|---|---|
| JP | 11-269138 | 10/1999 |
| JP | 2003012953 A * | 1/2003 |
| JP | 2003-212856 | 7/2003 |
| JP | 2003-535317 | 11/2003 |
| JP | 2005-264156 | 9/2005 |
| JP | 2006-36895 | 2/2006 |
| JP | 2007-241205 | 9/2007 |
| JP | 2008-247747 | 10/2008 |
| WO | 99/58517 | 11/1999 |
| WO | WO 01/84234 | 11/2001 |

OTHER PUBLICATIONS

Dörwald "Side Reactions in Organic Synthesis: A Guide to Successful Synthesis Design" 2005 Wiley-VCH Verlag GmbH & Co. KGaA, Wienheim.*

Suyama; Progress in Polymer Science 34 (2009) 194-209.*

Mochizuki et al; Macromolecules 1995,28, 365-369.*

Okada, Shigeto et al.: "(1-Pyrenyl)methyl carbamates for fluorescent "caged" amino acids and peptides", Photochemistry and Photobiology, 61(5), 431-4 CODEN: PHCBAP; ISSN: 0031-8655, 1955, XP00268770.

Habib Jiwan, J.L., et al., "Sol-gel silicate thin films bearing attached pyrene fluorescing probes hidden from oxygen but still accessible to organic electron transfer quenchers," Journal of Photochemistry and Photobiology A: Chemistry, vol. 122 (1999) p. 61-68.

Kornblum, N. and Scott, A., "A New Method for Protecting Amines," Journal of Organic Chemistry, vol. 42, No. 2 (1977) p. 399-400.

* cited by examiner

PHOTOBASE GENERATOR

TECHNICAL FIELD

The present invention relates to a compound which has a property of generating a base when irradiated with light (active energy rays), and a photobase generator containing the compound, in more detail, a high photosensitive compound having photosensitive range in 300 nm or longer wavelength, and a photobase generator containing the compound.

BACKGROUND OF THE INVENTION

Hardening by a photo (active energy rays)-sensitive polymerization initiator (hereinafter may be abbreviated only as a photo-polymerization initiator) (hereinafter the hardening may be abbreviated only as photo-hardening) has many advantages that hardening can be carried out at low temperature and for a short time, and can perform fine pattern formation and the like, comparing with hardening by a thermal-sensitive polymerization initiator (hereinafter may be abbreviated only as a thermal polymerization initiator) (hereinafter the hardening may be abbreviated only as thermal-hardening), therefore, it has been widely used in the application of surface processing such as coating materials, printing inks, dental materials, resists.

Photo-polymerization initiators to be used in the photo-hardening technology can be classified as 3 groups consisting of a photoradical generator, a photoacid generator, and a photobase generator according to the generated active species. The photoradical generator is a photo-polymerization initiator typically represented by acetophenone and the like which generates radical species when irradiated with light (active energy rays), and has been hitherto widely used. However, the radical species have a property of deactivating by oxygen in air, therefore, there is a disadvantage that the polymerization reaction is prohibited in the presence of oxygen, and hardening is consequently inhibited. Accordingly, when a thin film is hardened by using the photoradical generator, special device, by which oxygen is blocked in the air, is required. In addition, since the photoacid generator is the photo-polymerization initiator which generates an acid when irradiated with light (active energy rays), it has an advantage that it is not affected by inhibition due to oxygen, consequently, various photoacid generators have been used in practice since the latter half of the '90. However, when the generated acid by irradiated with light (active energy rays) is remained within system even after hardening, the problems that performance deterioration based on the denaturation of the hardened film and corrosion of the substrate in the semiconductor field and the like are pointed out. On the other hand, since the photobase generator is the photo-polymerization initiator which generates a base when irradiated with light (active energy rays), it has an advantage that it has not been affected by inhibition due to oxygen in the air, in addition, corrosion problem or denaturation of hardened film is hardly occurred. Therefore, this is the photo-polymerization initiator in which research and development thereof has been actively performed lately.

As such photobase generators, there are known various photobase generators, for example, such as a carbamate type (urethane type) photobase generator (for example, Patent Literature 1 and the like), an α-aminoketone type photobase generator (for example, Patent Literature 2 and the like), a quaternary ammonium type photobase generator (for example, Patent Literature 3, 4 and the like), an O-acyloxime type photobase generator (for example, Patent Literature 5 and the like).

On the other hand, an epoxy resin which is used as a photo-hardening resin has been hitherto hardened by graft polymerizing the epoxy resin by an acid generated from the acid generator by the action of light (active energy rays) under the coexistence of the resin and the acid generating-compound such as a photoacid generator. However, as mentioned above a little, when the acid is remained within the system even after hardening, problems of denaturing the hardened film or corroding the substrate due to the residual acid are occurred. For this reason, as the hardening method without occurring these problems, the method that the epoxy resin is hardened with a base, that is, the hardening of the epoxy resin by using the photobase generator is widely researched. However, at present, it is difficult situation of practical use due to the lack of sensitivity of the epoxy resin for the photobase generator. For this reason, research of a photo-hardening resin composition using an episulfide resin instead of the epoxy resin as the photo-hardening resin has been carried out (for example, Patent Literature 4 and the like). However, episulfide compounds as the episulfide resin precursor show the absorption in the vicinity of 300 nm wavelength. Therefore, when the photobase generator which has the same photosensitive range for the light (active energy rays) centered in the vicinity of 300 nm wavelength was used, there was a problem that generation efficiency of the base from the photobase generator decrease.

Under these circumstances, there has been expected the development of the photobase generator which eliminates overlap with the photo-absorption range of episulfide compounds, or even when overlapped, does not decrease the generation efficiency of the base, and can generate base efficiently, that is, the development of the photobase generator which has high sensitivity to longer wavelength light (active energy rays) comparing with the photosensitive range of the conventional photobase generator, and efficiently generates base when irradiated with the long wavelength light (active energy rays).

PRIOR ART LITERATURES

Patent Literatures

[PATENT LITERATURE 1] JP-A-10-77264
[PATENT LITERATURE 2] JP-A-11-71450
[PATENT LITERATURE 3] JP-A-2003-212856
[PATENT LITERATURE 4] JP-A-2005-264156
[PATENT LITERATURE 5] JP-A-2006-36895

DISCLOSURE OF INVENTION

Problem to be Solved by the Invention

A subject of the present invention is to provide a novel compound which easily generates a base even when irradiated with longer wavelength light (active energy rays) comparing with light (active energy rays) to which the conventional photobase generator is exposed, the photobase generator containing the compound and the base generation method.

Means to Solving the Problem

The present invention relates to the invention of a compound represented by the general formula [1]:

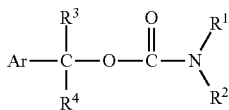

[1]

{wherein Ar represents any of groups selected from the group consisting of
an anthracenyl group represented by the general formula [I]:

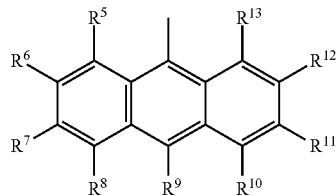

[I]

(wherein $R^5$ to $R^{13}$ each independently represent a hydrogen atom, a halogen atom, or a linear, branched or cyclic alkyl group having 1 to 10 carbon atoms),
an anthraquinonyl group represented by the general formula [II]:

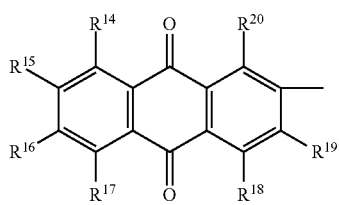

[II]

(wherein $R^{14}$ to $R^{20}$ each independently represent a hydrogen atom, a halogen atom, or a linear, branched or cyclic alkyl group having 1 to 10 carbon atoms), and
a pyrenyl group represented by the general formula [III]:

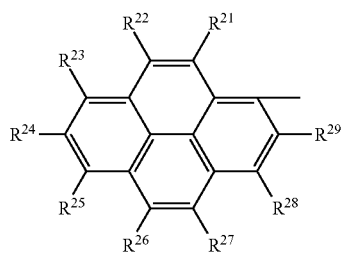

[III]

(wherein $R^{21}$ to $R^{29}$ each independently represent a hydrogen atom, a halogen atom, or a linear, branched or cyclic alkyl group having 1 to 10 carbon atoms), and
$R^1$ and $R^2$ each independently represent a hydrogen atom, or a linear, branched or cyclic alkyl group having 1 to 10 carbon atoms, or represent ones which can form an alicyclic ring containing nitrogen atom(s) or an aromatic ring containing nitrogen atom(s) together with a nitrogen atom to which these are bound, which the rings have 3 to 8 carbon atoms which may have a substituent, $R^3$ and $R^4$ each independently represent a hydrogen atom or a linear, branched or cyclic alkyl group having 1 to 10 carbon atoms}.

In addition, the present invention relates to the invention of a photobase generator containing the compound represented by the above-described general formula [1].

Further, the present invention relates to the invention of a base generating method characterized in that the compound represented by the above-described general formula [1] is irradiated with light.

Effect of the Invention

The compound of the present invention is the compound represented by the general formula [1], which efficiently generates base even when irradiated with longer wavelength light (active energy rays) comparing with the light (active energy rays) to which the conventional photobase generator is exposed. The compound has a property that effectively generates the base because it contains any of groups represented by the above-described general formula [I] to [III] which have the photo-sensitive range to light (active energy rays) of 300 nm or longer wavelength, and the urethane structure which efficiently release a(n) base (amine).

MODES FOR CARRYING-OUT OF THE INVENTION

Figure 1:
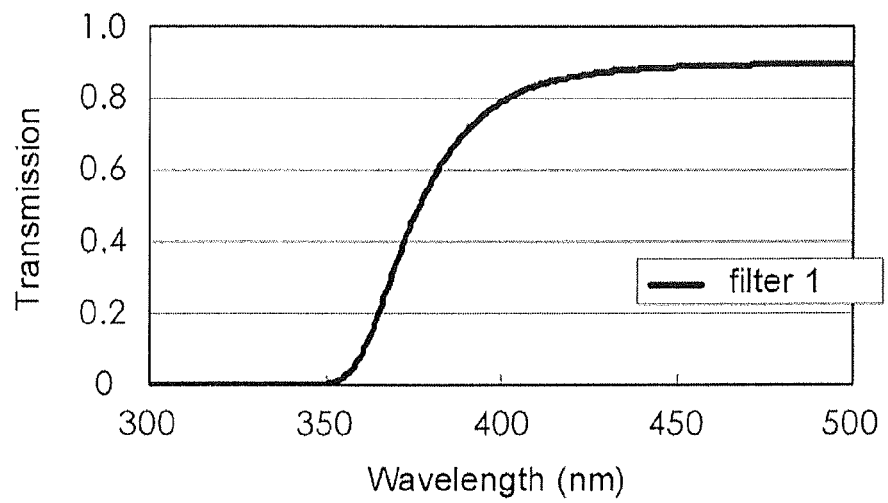
FIG. 1 is a drawing showing a transmissivity curve of filter-1 used in Example 14.
Figure 2:
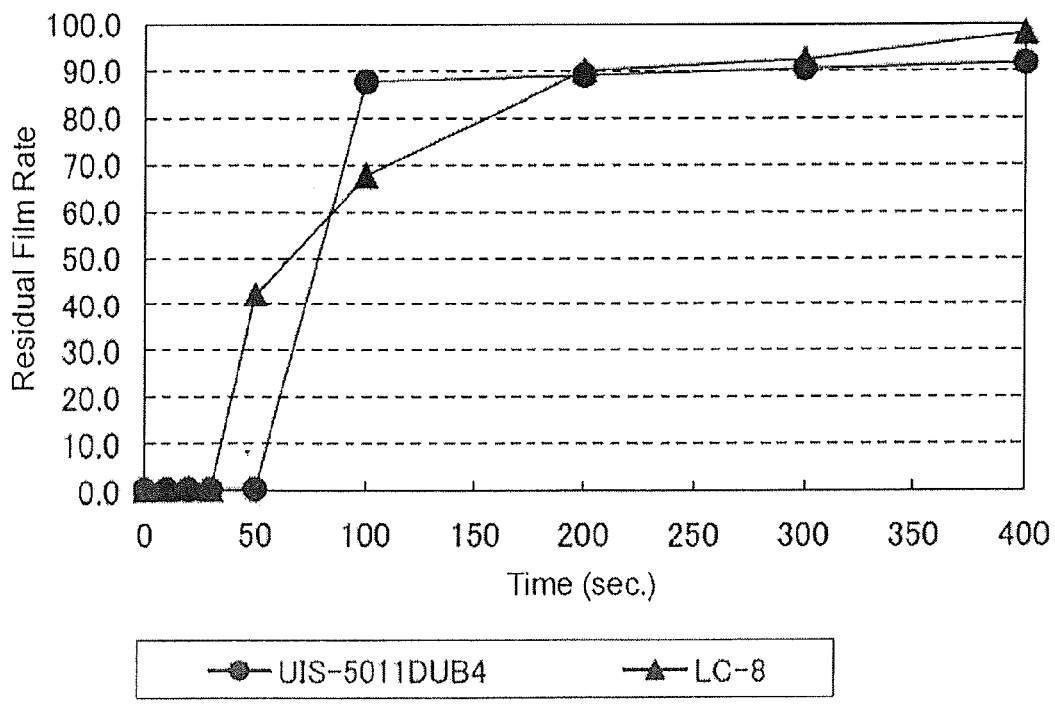
FIG. 2 is a drawing showing a relationship between irradiation time and rate of residual film, in the case where the coating film using a compound of Example 1 is irradiated with light (active energy rays) in Example 16.
Figure 3:
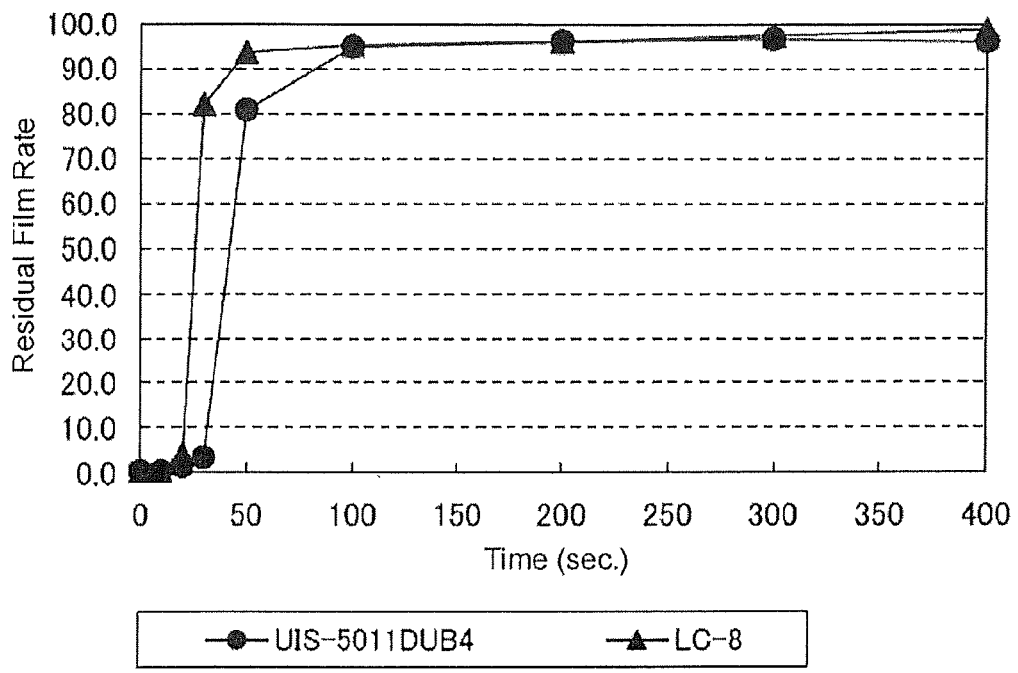
FIG. 3 is a drawing showing a relationship between irradiation time and rate of residual film, in the case where the coating film using a compound of Example 2 is irradiated with light (active energy rays) in Example 16.
Figure 4:
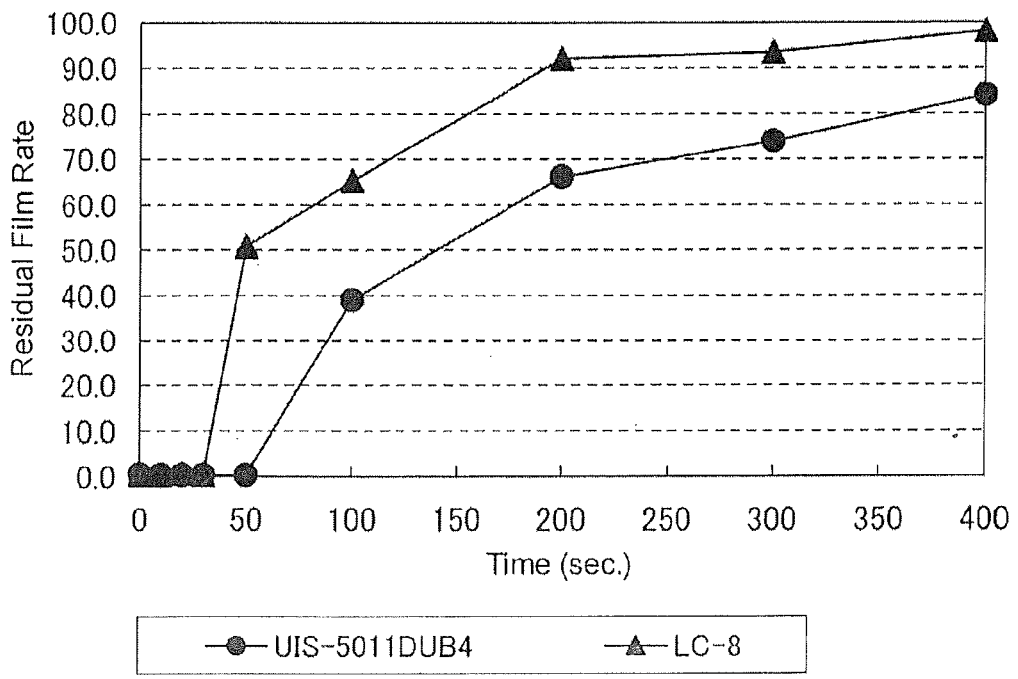
FIG. 4 is a drawing showing a relationship between irradiation time and rate of residual film, in the case where the coating film using a compound of Example 3 is irradiated with light (active energy rays) in Example 16.
Figure 5:
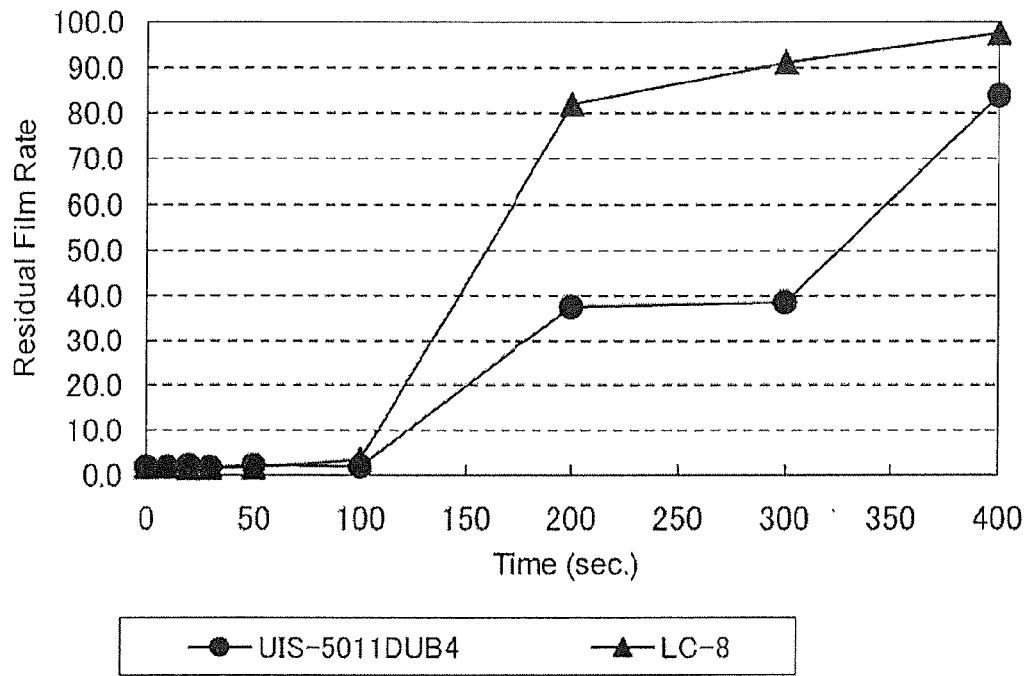
FIG. 5 is a drawing showing a relationship between irradiation time and rate of residual film, in the case where the coating film using a compound of Example 4 is irradiated with light (active energy rays) in Example 16.
Figure 6:
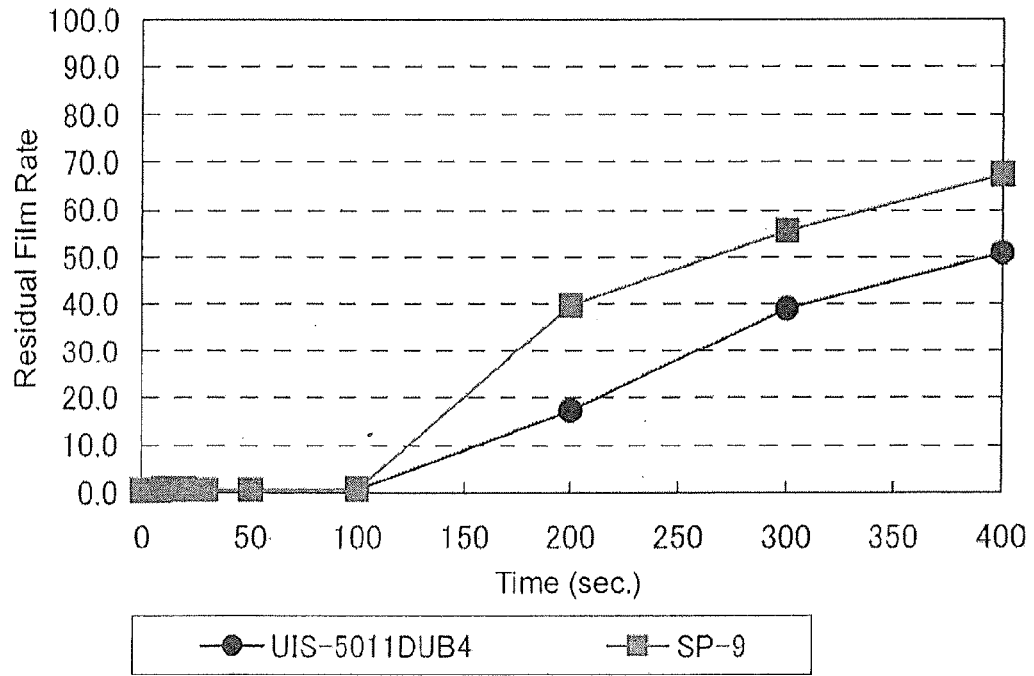
FIG. 6 is a drawing showing a relationship between irradiation time and rate of residual film, in the case where the coating film using a compound of Example 5 is irradiated with light (active energy rays) in Example 16.
Figure 7:
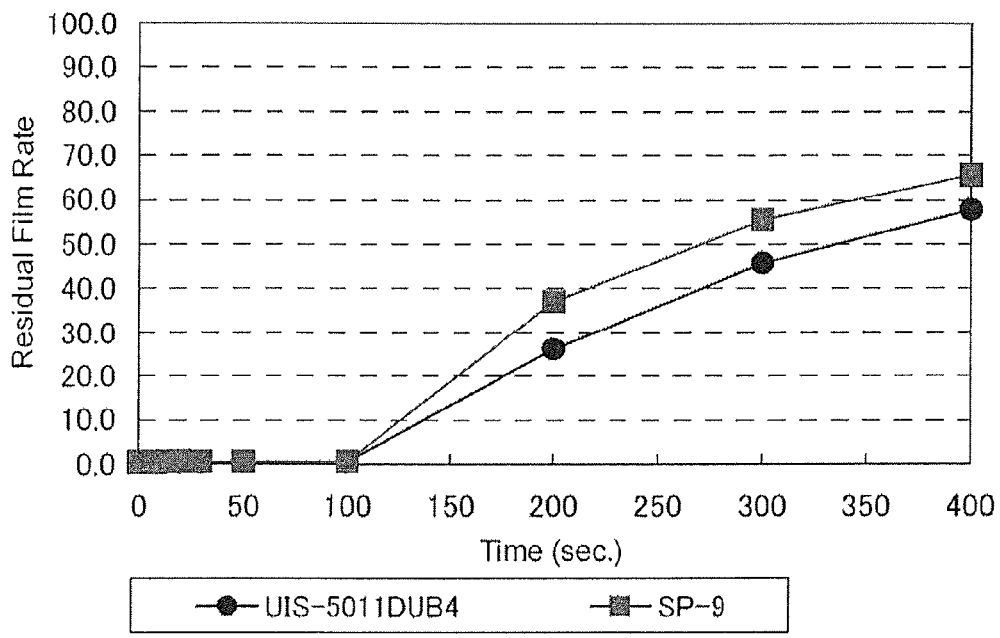
FIG. 7 is a drawing showing a relationship between irradiation time and rate of residual film, in the case where the coating film using a compound of Example 6 is irradiated with light (active energy rays) in Example 16.
Figure 8:
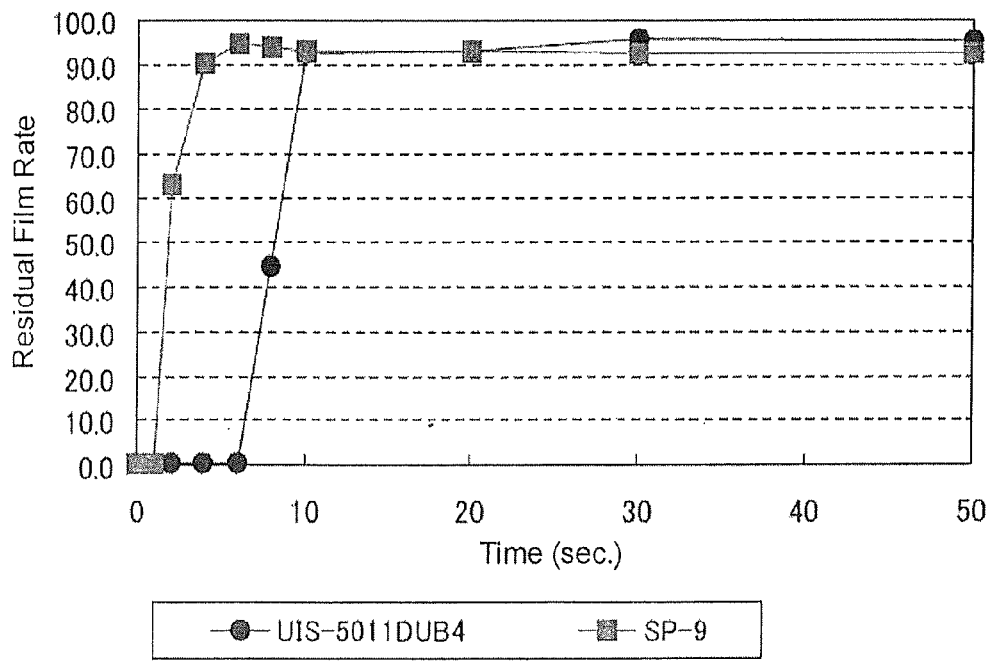
FIG. 8 is a drawing showing a relationship between irradiation time and rate of residual film, in the case where the coating film using a compound of Example 7 is irradiated with light (active energy rays) in Example 16.
Figure 9:
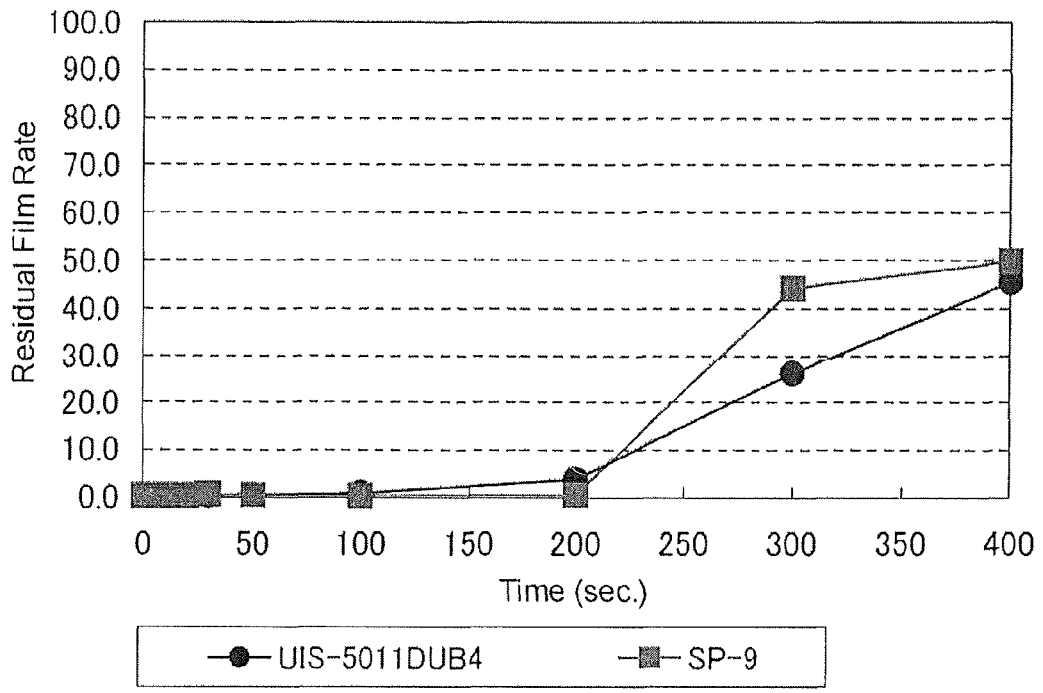
FIG. 9 is a drawing showing a relationship between irradiation time and rate of residual film, in the case where the coating film using a compound of Example 8 is irradiated with light (active energy rays) in Example 16.
Figure 10:
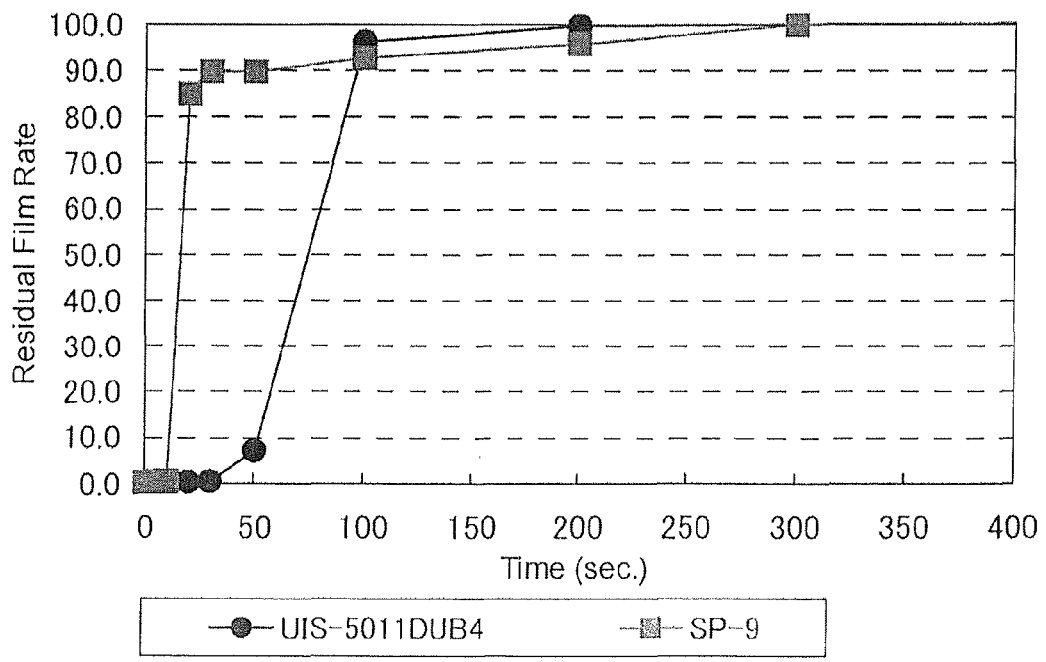
FIG. 10 is a drawing showing a relationship between irradiation time and rate of residual film, in the case where the coating film using a compound of Example 9 is irradiated with light (active energy rays) in Example 16.
Figure 11:
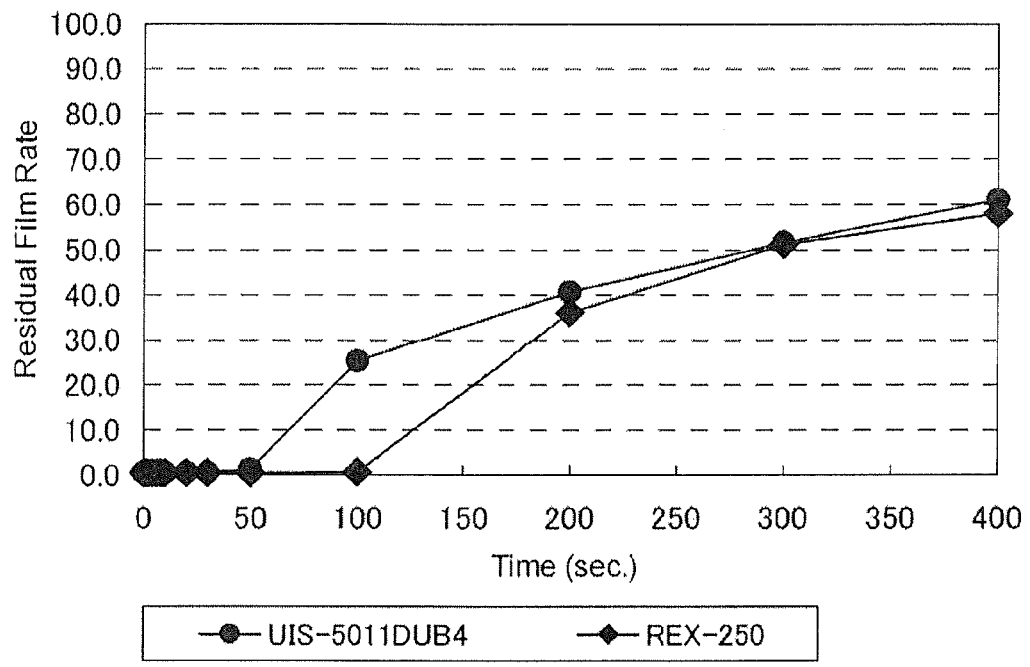
FIG. 11 is a drawing showing a relationship between irradiation time and rate of residual film, in the case where the coating film using a compound of Example 10 is irradiated with light (active energy rays) in Example 16.
Figure 12:
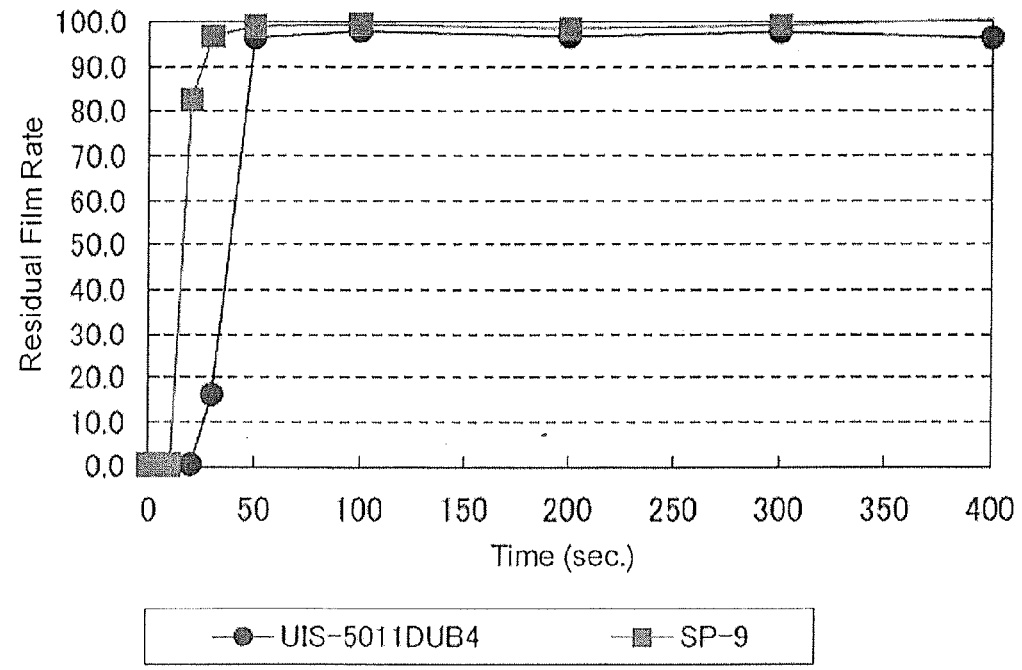
FIG. 12 is a drawing showing a relationship between irradiation time and rate of residual film, in the case where the coating film using a compound of Example 11 is irradiated with light (active energy rays) in Example 16.

The linear, branched, or cyclic alkyl groups having 1 to 10 carbon atoms represented by $R^1$ and $R^2$ in the general formula [1] include specifically, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group, an adamantyl group and the like; among them, the linear, branched, or cyclic alkyl groups having 1 to 8 carbon atoms are preferable, specifically, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group are preferable; among them, the linear or cyclic alkyl groups having 1 to 8 carbon atoms are more preferable, specifically, a methyl group, an ethyl group, a n-propyl group, a n-butyl group, a cyclobutyl group, n-pentyl group, a cyclopentyl group, a n-hexyl group, a cyclohexyl group, a n-heptyl group, a cycloheptyl group, a n-octyl group, a cyclooctyl group are more preferable; further among them, the linear or cyclic alkyl groups having 1 to 6 carbon atoms are further preferable, specifically, a methyl group, an ethyl group, a n-propyl group, a n-butyl group, a cyclobutyl group, a n-pentyl group, a cyclopentyl group, a n-hexyl group, a cyclohexyl group are further preferable.

In "ones which form an alicyclic ring containing nitrogen atom(s) or an aromatic ring containing nitrogen atom(s) together with a nitrogen atom to which they ($R^1$ and $R^2$) are bound, which the rings have 3 to 8 carbon atoms which may have a substituent" represented by $R^1$ and $R^2$ in the general formula [1], "to form an alicyclic ring containing nitrogen atom(s) or an aromatic ring containing nitrogen atom(s) which the rings have 3 to 8 carbon atoms" means to form a saturated or an unsaturated alkylene group (a saturated or an unsaturated alkanediyl group) bound to the nitrogen atom to which through 2 bonds provided by linkage with $R^1$ and $R^2$, more specifically, means to form a saturated or an unsaturated alkylene group (a saturated or an unsaturated alkanediyl group) having 3 to 8 carbon atoms, wherein hetero atom(s) may be contained in the chain. Specific examples of the above-described the saturated or the unsaturated alkylene groups (the saturated or the unsaturated alkanediyl groups) having 3 to 8 carbon atoms wherein hetero atom may be contained in the chain include, for example, the linear or branched, saturated alkylene groups (the saturated alkanediyl groups) having 3 to 8 carbon atoms, wherein no-hetero atom is contained in the chain such as a trimethylene group, a tetramethylene group, a pentamethylene group, a hexamethylene group, a heptamethylene group, an octamethylene group, a 1,4-dimethyltetramethylene group, a 1,5-dimethylpentamethylene group, a 1,3,5-trimethylpentamethylene group; for example, the linear or branched, saturated alkylene groups (saturated alkanediyl groups) having 3 to 8 carbon atoms, wherein hetero atom(s) (an oxygen atom, a sulfur atom and the like) is contained in the chain such as a methyleneoxydimethylene group (a methyleneoxyethylene group), a methylenethiodimethylene group (a methylenethioethylene group), a dimethyleneoxydimethylene group (an ethyleneoxyethylene group), a dimethylenethiodimethylene group (an ethylenethioethylene group), a 1,1',2-trimethyl-methyleneoxydimethylene group (a 1,1',2-trimethyl-methyleneoxyethylene group), a 1,1',2-trimethyl-methylenethiodimethylene group (a 1,1',2-trimethyl-methylenethioethylene group), a 1,1',2,2'-tetramethyl-dimethyleneoxydimethylene group (a 1,1',2,2'-tetramethyl-ethyleneoxyethylene group), a 1,1',2,2'-tetramethyl-dimethylenethiodimethylene group (a 1,1',2,2'-tetramethyl-ethylenethioethylene group); for example, the linear or branched, unsaturated alkylene groups (the unsaturated alkanediyl groups) having 4 to 8 carbon atoms, wherein no-hetero atom is contained in the chain such as a but-1,3-diene-1,4-diyl group, a 1,4-dimethyl-but-1,3-diene-1,4-diyl group, a 1,4-diethyl-but-1,3-diene-1,4-diyl group; for example, the linear or branched, unsaturated alkylene groups (the unsaturated alkanediyl groups) having 3 to 8 carbon atoms, wherein hetero atom(s) (a nitrogen atom and the like) is contained in the chain such as a 2-aza-but-1,3-diene-1,4-diyl group, a 1,4-dimethyl-2-aza-but-1,3-diene-1,4-diyl group, a 1,4-diethyl-2-aza-but-1,3-diene-1,4-diyl group, a 1-aza-but-1,3-diene-1,4-diyl group, a 2,4-dimethyl-1-aza-but-1,3-diene-1,4-diyl group, a 2,4-diethyl-1-aza-but-1,3-diene-1,4-diyl group.

In these saturated or unsaturated alkylene groups (the saturated or unsaturated alkanediyl groups), for example, the linear saturated alkylene groups (the saturated alkanediyl groups) having 4 to 7 carbon atoms, wherein no hetero atom is contained in the chain such as a tetramethylene group, a pentamethylene group, a hexamethylene group, a heptamethylene group; for example, the linear saturated alkylene groups (the saturated alkanediyl groups) having 3 to 4 carbon atoms, wherein hetero atom(s) (an oxygen atom, a sulfur atom and the like) is contained in the chain such as a methyleneoxydimethylene group (a methyleneoxyethylene group), a methylenethiodimethylene group (a methylenethioethylene group), a dimethyleneoxydimethylene group (an ethyleneoxyethylene group), a dimethylenethiodimethylene group (an ethylenethioethylene group); the linear unsaturated alkylene groups (the unsaturated alkanediyl groups) having 4 carbon atoms, wherein no hetero atom is contained in the chain such as a but-1,3-diene-1,4-diyl group; the linear unsaturated alkylene groups (the unsaturated alkanediyl groups) having 3 carbon atoms, wherein hetero atom(s) (a nitrogen atom and the like) is contained in the chain such as a 2-azabut-1,3-diene-1,4-diyl group, a 1-aza-but-1,3-diene-1,4-diyl group are preferable; furthermore, among them, the linear saturated alkylene groups (the saturated alkanediyl groups) having 4 to 5 carbon atoms, wherein no hetero atom is contained in the chain such as a tetramethylene group, a pentamethylene group; the linear saturated alkylene groups (the saturated alkanediyl groups) having 4 carbon atoms, wherein hetero atom(s) (an oxygen atom, a sulfur atom and the like) is contained in the chain such as a dimethyleneoxydimethylene group (an ethyleneoxyethylene group), a dimethylethiodimethylene group (an ethylenethioethylene group) are more preferable.

In "ones which form an alicyclic ring containing nitrogen atom(s) or an aromatic ring containing nitrogen atom(s) together with a nitrogen atom to which they ($R^1$ and $R^2$) are bound, which the rings have 3 to 8 carbon atoms which may have a substituent" represented by $R^1$ and $R^2$ in the general formula [1], "substituents", specifically, include, for example, substituents (functional groups) other than hydrocarbon groups, bound to the above-described "ones which form a nitrogen containing alicyclic ring or a nitrogen containing aromatic ring" such as a hydroxyl group, a mercapto group, a cyano group, a nitro group, for example, halogen atoms such as a fluorine atom, a chlorine atom, a bromine atom, an iodine atom. Therefore, in the present invention, number of the carbon atoms in "ones which form an alicyclic ring containing nitrogen atom(s) or an aromatic ring containing nitrogen atom(s) which the rings have 3 to 8 carbon atoms which may have a substituent" means number of carbon atoms in the moiety forming an alicyclic ring containing nitrogen atom(s) or an aromatic ring containing nitrogen atom(s), and the number of carbon atoms in the above-described substituents (a cyano group and the like) is excluded.

As the $R^1$ and $R^2$ in the general formula [1], ones are more preferable that $R^1$ is a hydrogen atom, $R^2$ is a linear or cyclic alkyl group having 3 to 8 carbon atoms; $R^1$ and $R^2$ are both linear alkyl groups having 1 to 8 carbon atoms; $R^1$ and $R^2$ form an alicyclic ring containing nitrogen atom(s) or an aromatic ring containing nitrogen atom(s) together with a nitrogen atom to which they are bound, which the rings have 3 to 7 carbon atoms which may have a substituent, among them, ones are further preferable that $R^1$ is a hydrogen atom, $R^2$ is a linear or cyclic alkyl group having 3 to 6 carbon atoms; $R^1$ and $R^2$ are both linear alkyl groups having 1 to 6 carbon atoms; $R^1$ and $R^2$ form an alicyclic ring containing nitrogen atom(s) together with a nitrogen atom to which they are bound, which the ring has 4 to 5 carbon atoms which may have a substituent.

The linear, branched or cyclic alkyl groups having 1 to 10 carbon atoms represented by $R^3$ and $R^4$ in general formula [1] include, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group, an adamantyl group and the like, among them, the linear alkyl groups having 1 to 3 carbon atoms are preferable, specifically, a methyl group, an ethyl group, a n-propyl group are preferable, among them, the alkyl group having 1 carbon atom, i.e. a methyl group is more preferable.

As the $R^3$ and $R^4$ in the general formula [1], a hydrogen atom, a methyl group are more preferable.

The anthracenyl group represented by the above-described general formula [I], the anthraquinonyl group represented by the above-described general formula [II], the pyrenyl group represented by the above-described general formula [III], which are shown as Ar group in the compound represented by the general formula [1] of the present invention can more efficiently absorb long wavelength light (active energy rays), therefore, by selecting any group selected from them, i.e. the specific tri- or tetra-cyclic aromatic hydrocarbon group, the compound of the present invention can become the photobase generator which can efficiently generate a base even by irradiated with longer wavelength light (active energy rays) comparing with light (active energy rays) to which the conventional photobase generator is exposed.

The halogen atoms represented by $R^5$ to $R^{29}$ in the above-described general formula [I], [II], and [III], specifically, include, for example, a fluorine atom, a chlorine atom, a bromine atom, an iodine atom and the like, among them, a chlorine atom, a bromine atom are preferable, further among them, a bromine atom is more preferable.

The linear, branched or cyclic alkyl groups having 1 to 10 carbon atoms represented by $R^5$ to $R^{29}$ in the above-described general formula [I], [II], and [III], specifically, include, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group, an adamantyl group and the like, among them, a linear alkyl group having 1 to 3 carbon atoms is preferable, specifically, a methyl group, an ethyl group, a n-propyl group are preferable, among them, an alkyl group having 1 carbon atom, i.e. a methyl group is more preferable.

As the $R^5$ to $R^{29}$ in the above-described general formula [I], [II] and [III], a hydrogen atom, a halogen atom are more preferable, among them, a hydrogen atom is further preferable.

In the compound represented by the general formula [1] of the present invention, structure of amine moiety in the case where $R^1$ and $R^2$ is "ones in which $R^1$ and $R^2$ form an alicyclic ring containing nitrogen atom(s) or an aromatic ring containing nitrogen atom(s) together with a nitrogen atom to which they ($R^1$ and $R^2$) are bound, which the rings have 3 to 8 carbon atoms which may have a substituent", that is, specific examples of "an alicyclic ring containing nitrogen atom(s) or an aromatic ring containing nitrogen atom(s) which the rings have 3 to 8 carbon atoms" include, for example, an alicyclic ring containing a nitrogen atom which the ring has, 3 to 8 carbon atoms such as an azetidine ring (a 4-membered ring), a pyrrolidine ring (a 5-membered ring), a piperidine ring (a 6-membered ring), a hexamethyleneimine ring (an azepane ring; a 7-membered ring), a heptamethyleneimine ring (an azocane ring; a 8-membered ring), an octamethyleneimine ring (an azonane ring; a 9-membered ring); for example, an alicyclic ring containing a nitrogen atom which the ring has 3 to 8 carbon atoms, wherein hydrogen atoms bound to carbon atoms constituting an alicyclic ring are substituted by methyl groups, such as a 2,5-dimethylpyrrolidine ring (a 5-membered ring), a 2,6-dimethylpiperidine ring (a 6-membered ring), a 2,4,6-trimethylpiperidine ring (a 6-membered ring); for example, an alicyclic ring containing nitrogen atom(s) which the ring has 3 to 8 carbon atoms, wherein hetero atom(s) other than the nitrogen atom(s) (an oxygen atom, a sulfur atom and the like) is contained in the chain, such as an oxazolidine ring (a 5-membered ring), a thiazolidine ring (a 5-membered ring), a morpholine ring (a 6-membered ring), a thiomorpholine ring (a 6-membered ring); for example, an alicyclic ring containing nitrogen atom(s) which the ring has 4 to 8 carbon atoms, wherein hetero atom(s) other than nitrogen atom(s) (an oxygen atom, a sulfur atom and the like) is contained in the chain, and hydrogen atoms bound to carbon atoms constituting an alicyclic ring are substituted by methyl groups, such as a 2,3,5,6-tetramethylmorpholine (a 6-membered ring), a 2,3,5,6-tetramethylthiomorpholine (a 6-membered ring); for example, an aromatic ring containing nitrogen atom(s) which the ring has 3 to 4 carbon atoms such as a pyrrole ring (a 5-membered ring), an imidazole ring (a 5-membered ring), a pyrazole ring (a 5-membered ring); for example, an aromatic ring containing nitrogen atom(s) having 4 to 8 carbon atoms, wherein hydrogen atoms bound to carbon atoms constituting an aromatic ring are substituted by methyl groups or ethyl groups, such as a 2,5-dimethylpyrrole ring (a 5-membered ring), a 2,5-diethylpyrrole ring (a 5-membered ring), a 2,5-dimethyl imidazole ring (a 5-membered ring), a 2,5-diethyl imidazole ring (a 5-membered ring), a 3,5-dimethylpyrazole ring (a 5-membered ring), a 3,5-diethylpyrazole ring (a 5-membered ring). That is, an alicyclic ring containing nitrogen atom(s) or an aromatic ring containing nitrogen atom(s) which the rings have 3 to 8 carbon atoms, wherein hydrogen atoms bound to carbon atoms constituting an alicyclic ring or an aromatic ring are substituted by methyl groups or ethyl groups; an alicyclic ring containing nitrogen atom(s) which the ring have 3 to 8 carbon atoms, wherein hetero atom(s) other than nitrogen atom(s) (an oxygen atom, a sulfur atom and the like) is contained in the chain, are contained in the above-described concept of "an alicyclic ring containing nitrogen atom(s) or an aromatic ring containing nitrogen atom(s) which the rings have 3 to 8 carbon atoms".

In these "alicyclic rings containing nitrogen atom(s) or aromatic rings containing nitrogen atom(s) which the rings have 3 to 8 carbon atoms", for example, an alicyclic ring containing a nitrogen atom which the ring has 4 to 7 carbon atoms, wherein no hetero atom other than a nitrogen atom is contained in the chain, and a hydrogen atom bound to a carbon atom constituting an alicyclic ring is not substituted by a methyl group, such as a pyrrolidine ring (a 5-membered ring), a piperidine ring (a 6-membered ring), a hexamethyleneimine ring (an azepane ring; a 7-membered ring), a heptamethyleneimine ring (an azocane ring; a 8-membered ring); for example, an alicyclic ring containing a nitrogen atom which the ring has 3 to 4 carbon atoms, wherein hetero atom(s) other than a nitrogen atom (an oxygen atom, a sulfur atom and the like) is contained in the chain, and a hydrogen atom bound to a carbon atom constituting an alicyclic ring is not substituted by a methyl group, such as an oxazolidine ring (a 5-membered ring), a thiazolidine ring (a 5-membered ring), a morpholine ring (a 6-membered ring), a thiomorpholine ring (a 6-membered ring); for example, an aromatic ring containing nitrogen atom(s) which the ring has 3 to 4 carbon atoms, wherein a hydrogen atom bound to a carbon atom constituting an aromatic ring is not substituted by a methyl group or an ethyl group such as a pyrrole ring (a 5-membered ring), an imidazole ring (a 5-membered ring), a pyrazole ring (a 5-membered ring) are preferable, further among them, for example, an alicyclic ring containing a nitrogen atom which the ring has 4 to 5 carbon atoms, wherein no hetero atom other than a nitrogen atom is contained in the chain, and a hydrogen atom bound to a carbon atom constituting an alicyclic ring is not substituted by a methyl group, such as a pyrrolidine ring (a 5-membered ring), a piperidine ring (a 6-membered ring); for example, an alicyclic ring containing a nitrogen atom which the ring has 4 carbon atoms, wherein hetero atom(s) (an oxygen atom, a sulfur atom and the like) other than a nitrogen atom is contained in the chain, and a hydrogen atom bound to a carbon atom constituting an alicyclic ring is not substituted by a methyl group, such as a morpholine ring (a 6-membered ring), a thiomorpholine ring (a 6-membered ring) are more preferable. The compounds represented by the general formula [1] which have "an alicyclic ring containing a nitrogen atom which the ring has 4 to 7 carbon atoms, wherein no hetero atom other than a nitrogen atom is contained in the chain, and a hydrogen atom bound to a carbon atom constituting an alicyclic ring is not substituted by a methyl group", "an alicyclic ring containing a nitrogen atom which the ring has 3 to 4 carbon atoms, wherein hetero atom(s) other than a nitrogen atom (an oxygen atom, a sulfur atom and the like) is contained in the chain, and a hydrogen atom bound to a carbon atom constituting an alicyclic ring is not substituted by a methyl group", or "an aromatic ring containing nitrogen atom(s) which the ring has 3 to 4 carbon atoms, wherein a hydrogen atom bound to a carbon atom constituting an aromatic ring is not substituted by a methyl group or an ethyl group" of these preferable specific examples, are useful from the viewpoint that they can be inexpensively and easily produced, and can efficiently generate a base when irradiated with light (active energy rays).

The above-mentioned "an alicyclic ring containing nitrogen atom(s) or an aromatic ring containing nitrogen atom(s) which the rings have 3 to 8 carbon atoms" may further have a substituent (a functional group) other than a hydrocarbon group, and specific examples of the substituents, as described above, include, for example, a hydroxyl group, a mercapto group, a cyano group, a nitro group, for example, halogen atoms such as a fluorine atom, a chlorine atom, a bromine atom, an iodine atom. Specific examples of "an alicyclic ring containing nitrogen atom(s) or an aromatic ring containing nitrogen atom(s) which the rings have 3 to 8 carbon atoms" which may have the above-described "substituents" include, for example, a 4-hydroxypiperidine ring (a 6-membered ring), a 4-mercaptopiperidine ring (a 6-membered ring), a 4-cyanopiperidine ring (a 6-membered ring), a 4-nitropiperidine ring (a 6-membered ring), a 4-chloropiperidine ring (a 6-membered ring), a 4-bromopiperidine ring (a 6-membered ring), however, is not limited to any of these examples.

More specific compounds in these compounds represented by the above-described general formula [1] of the present invention, include ones that $R^5$ to $R^{29}$ in the above-described general formula [I] to [III] represented by Ar in the general formula [1], are each independently a hydrogen atom or a halogen atom, $R^1$ and $R^2$ are both a linear alkyl group having 1 to 8 carbon atoms, and $R^3$ and $R^4$ are each independently a hydrogen atom or a linear alkyl group having 1 to 3 carbon atoms, and ones represented by the general formula [2]:

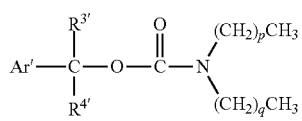

[2]

{wherein, Ar' represents any of groups selected from the group consisting of
an anthracenyl group represented by the general formula [I']:

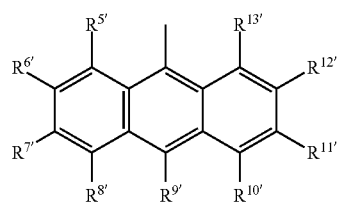

[I']

(wherein, $R^{5\prime}$ to $R^{13\prime}$ each independently represent a hydrogen atom or a halogen atom);
an anthraquinonyl group represented by the general formula [II']:

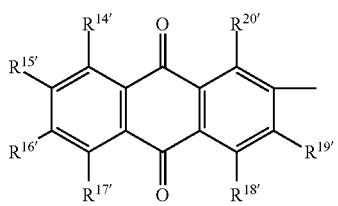

[II']

(wherein, $R^{14\prime}$ to $R^{20\prime}$ each independently represent a hydrogen atom or a halogen atom); and
a pyrenyl group represented by the general formula [III']:

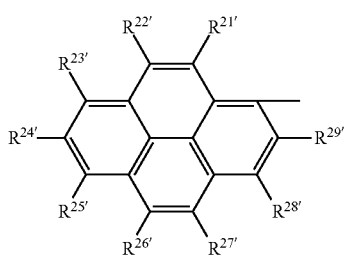

[III']

(wherein, $R^{21\prime}$ to $R^{29\prime}$ each independently represent a hydrogen atom or a halogen atom), $R^{3\prime}$ and $R^{4\prime}$ each independently represent a hydrogen atom or a linear alkyl group having 1 to 3 carbon atoms, p and q each independently represent an integer of 0 to 7}; ones that $R^5$ to $R^{29}$ in the above-described general formula [I] to [III] represented by Ar in the general formula [1], are each independently a hydrogen atom or a halogen atom, $R^1$ and $R^2$ are ones which form an alicyclic ring containing a nitrogen atom together with a nitrogen atom to which they ($R^1$ and $R^2$) are bound, which the ring has 4 to 7 carbon atoms, wherein a substituent is not contained, and also no hetero atom other than a nitrogen atom is contained in the chain, and a hydrogen atom bound to a carbon atom constituting an alicyclic ring is not substituted by a methyl group, and $R^3$ and $R^4$ are each independently a hydrogen atom or a linear alkyl group having 1 to 3 carbon atoms, and ones represented by the general formula [3]:

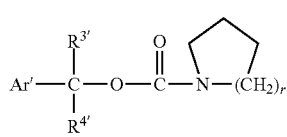

[3]

(wherein, r represents an integer of 1 to 4, Ar', $R^{3\prime}$ and $R^{4\prime}$ are the same as above); ones that $R^5$ to $R^{29}$ in the above-described general formula [I] to [III] represented by Ar in the general formula [1], are each independently a hydrogen atom or a halogen atom, $R^1$ is a hydrogen atom, $R^2$ is a linear or cyclic alkyl group having 3 to 8 carbon atoms, and $R^3$ and $R^4$ are each independently a hydrogen atom, or a linear alkyl group having 1 to 3 carbon atoms, and ones represented by the general formula [4]:

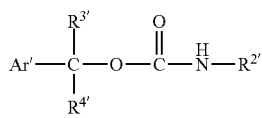

[4]

(wherein, $R^{2\prime}$ represents a linear or cyclic alkyl group having 3 to 8 carbon atoms, Ar', $R^{3\prime}$ and $R^{4\prime}$ are the same as above); ones that $R^5$ to $R^{29}$ in the above-described general formula [I] to [III] represented by Ar in the general formula [1], are each independently a hydrogen atom or a halogen atom, $R^1$ and $R^2$ are ones which form an alicyclic ring containing a nitrogen atom together with a nitrogen atom to which they ($R^1$ and $R^2$) are bound, which the ring has 5 carbon atoms, wherein a substituent is contained, and also no hetero atom other than a nitrogen atom is contained in the chain, and a hydrogen atom bound to a carbon atom constituting an alicyclic ring is not substituted by a methyl group, and $R^3$ and $R^4$ are each independently a hydrogen atom or a linear alkyl group having 1 to 3 carbon atoms, and ones represented by the general formula [5]:

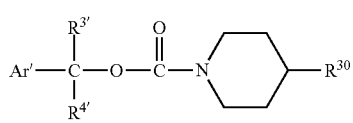

[5]

(wherein, $R^{30}$ represents a hydroxyl group, a mercapto group, a cyano group, a nitro group or a halogen atom, Ar', $R^{3\prime}$ and $R^{4'}$ are the same as above). These compounds are preferable from the viewpoint that they can be inexpensively and easily produced comparing with the other compounds of the present invention, furthermore, heat-resistance thereof can be expected, and they can become the photobase generator which can more efficiently generate a base even when irradiated with longer wavelength light (active energy rays) comparing with the light (active energy rays) to which the conventional photobase generator is exposed.

The linear alkyl groups having 1 to 3 carbon atoms represented by $R^{3'}$ and $R^{4'}$ in the above-described general formula [2], [3], [4] and [5], specifically include, for example, a methyl group, an ethyl group, a n-propyl group and the like, among them, an alkyl group having 1 carbon atom, i.e. a methyl group is preferable.

As the $R^{3'}$ and $R^{4'}$ in the above-described general formula [2], [3], [4] and [5], the combination that $R^{3'}$ and $R^{4'}$ are both a hydrogen atom, the combination that $R^{3'}$ is a hydrogen atom, and $R^{4'}$ is a methyl group, the combination that $R^{3'}$ and $R^{4'}$ are both a methyl group are more preferable, among them, the combination that $R^{3'}$ and $R^{4'}$ are both a hydrogen atom, the combination that $R^{3'}$ is a hydrogen atom, and $R^{4'}$ is a methyl group are further preferable, furthermore among them, the combination that $R^{3'}$ and $R^{4'}$ are both a hydrogen atom is particularly preferable.

The halogen atoms represented by $R^{5'}$ to $R^{29'}$ in the above-described general formula [I'], [II'] and [III'] include, for example, a fluorine atom, a chlorine atom, a bromine atom, an iodine atom and the like, among them, a chlorine atom, a bromine atom are preferable, furthermore, a bromine atom is more preferable.

The $R^{5'}$ to $R^{8'}$ and $R^{10'}$ to $R^{29'}$ in the above-described general formula [I'], [II'] and [III'] are preferably a hydrogen atom. That is, in the groups represented by Ar' in the above-described general formula [2], [3], [4] and [5], any of groups selected from the group consisting of an anthracenyl group represented by the general formula [I"]:

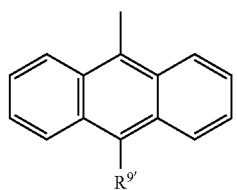

(wherein, $R^{9'}$ is the same as above);

an anthraquinonyl group represented by the formula [V]:

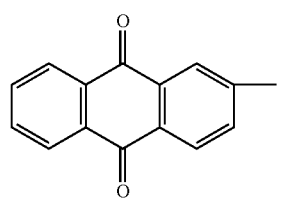

a pyrenyl group represented by the formula [VI]:

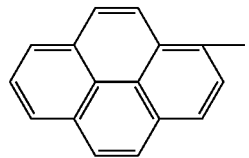

are preferable. Further, in the group represented by the general formula [I"], the group that $R^{9'}$ is a hydrogen atom, i.e. an anthracenyl group represented by the formula [IV] is further preferable.

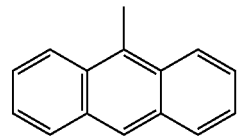

As the p and q in the above-described general formula [2], integers of 0 to 7 are more preferable, among them, integers of 0 to 5 are further preferable, further among them, 1 is particularly preferable. Thus, the compounds in which the p and q are integers of 0 to 5, i.e. the compounds, which generate a linear chain dialkylamine having 1 to 6 carbon atoms as a base, is the preferable compounds from the viewpoint that the amine has appropriate nucleophilicity because bulkiness of the amine is not so large, in addition, the amine is less evaporative when heat-processing in film formation of an epoxy resin and the like, because boiling point of the amine is comparatively high, therefore, effective patterning can be carried out.

As the r in the above-described general formula [3], an integer of 1 to 2 is more preferable, among them, 2 is further preferable.

The linear or cyclic alkyl groups having 3 to 8 carbon atoms represented by $R^{2'}$ in the above-described general formula [4], specifically, include, for example, a n-propyl group, a n-butyl group, a cyclobutyl group, a n-pentyl group, a cyclopentyl group, a n-hexyl group, a cyclohexyl group, a n-heptyl group, a cycloheptyl group, a n-octyl group, a cyclooctyl group and the like, among them, the linear or cyclic alkyl groups having 3 to 6 carbon atoms are preferable, specifically, a n-propyl group, a n-butyl group, a cyclobutyl group, a n-pentyl group, a cyclopentyl group, a n-hexyl group, a cyclohexyl group are preferable.

The halogen atoms represented by $R^{30}$ in the above-described general formula [5], include, for example, a fluorine atom, a chlorine atom, a bromine atom, an iodine atom and the like, among them, a chlorine atom, a bromine atom are preferable.

As the $R^{30}$ in the above-described general formula [5], a hydroxyl group is more preferable.

More preferable specific examples of the compounds represented by the above-described general formula [2] include ones that Ar' in the general formula [2] is an anthracenyl group represented by the above-described general formula [I"], wherein $R^{9'}$ in the general formula [I"] is a hydrogen atom or a bromine atom, $R^{3'}$ and $R^{4'}$ are both a hydrogen atom, and p and q are both 1, more specifically, the compound represented by the formula [7]:

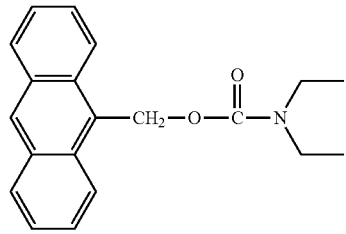

[7]

and the compound represented by the formula [8]:

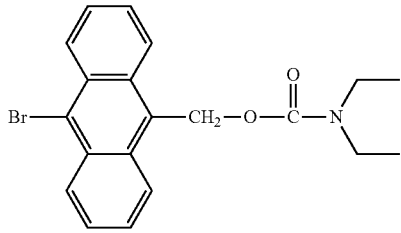

[8]

can be more preferably exemplified.

Furthermore, in addition, for confirmation, the compounds represented by the above-described formula [7] correspond to ones that Ar in the above-described general formula [1] is an anthracenyl group represented by the above-described general formula [I], all of $R^5$ to $R^{13}$ in the general formula [I] are a hydrogen atom, $R^1$ and $R^2$ are both an alkyl group having 2 carbon atoms, i.e. an ethyl group, and $R^3$ and $R^4$ are both a hydrogen atom.

Also, in addition, for confirmation, the compounds represented by the above-described formula [8] correspond to ones that Ar in the above-described general formula [1] is an anthracenyl group represented by the above-described general formula [I], all of $R^5$ to $R^8$ and $R^{10}$ to $R^{13}$ in the general formula [I] are a hydrogen atom, and also, $R^9$ is a bromine atom, $R^1$ and $R^2$ are both an alkyl group having 2 carbon atoms, i.e. an ethyl group, and $R^3$ and $R^4$ are both a hydrogen atom.

In addition, more preferable specific compounds represented by the above-described general formula [3] include ones that Ar' in the general formula [3] is any of groups selected from the group consisting of an anthracenyl group represented by the above-described formula [IV]; an anthraquinonyl group represented by the above-described formula [V]; and a pyrenyl group represented by the above-described formula [VI], $R^{3'}$ and $R^{4'}$ are both a hydrogen atom, or $R^{3'}$ is a hydrogen atom, $R^{4'}$ is a methyl group, and r is 2, more specifically, the compound represented by the formula [10]:

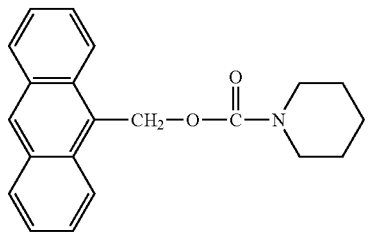

[10]

the compound represented by the formula [11]:

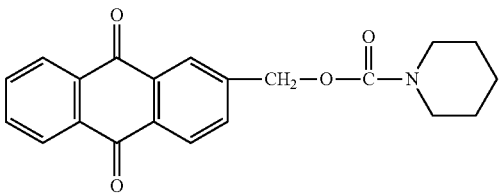

[11]

the compound represented by the formula [12]:

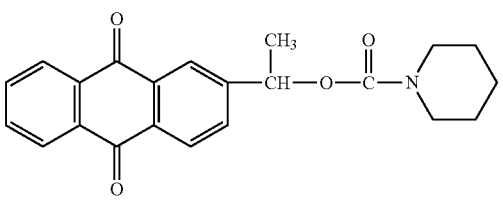

[12]

the compound represented by the formula [13]:

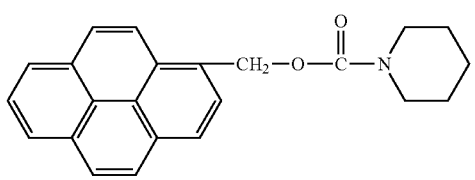

[13]

can be more preferably exemplified.

Furthermore, in addition, for confirmation, the compounds represented by the above-described formula [10], [11] and [13] correspond to ones that Ar in the above-described general formula [1] is any of groups selected from the group consisting of an anthracenyl group represented by the above-described general formula [I]; an anthraquinonyl group represented by the above-described general formula [II]; and a pyrenyl group represented by the above-described general formula [III], and all of $R^5$ to $R^{29}$ in the general formula [I] to [III] are a hydrogen atom, $R^1$ and $R^2$ are ones which form an alicyclic ring containing a nitrogen atom together with a nitrogen atom to which they ($R^1$ and $R^2$) are bound, which the ring have 5 carbon atoms, wherein a substituent is not contained, and also, no hetero atom other than a nitrogen atom is contained in the chain, and a hydrogen atom bound to a carbon atom constituting an alicyclic ring is not substituted by a methyl group, i.e. a piperidine ring, and $R^3$ and $R^4$ are both a hydrogen atom.

Also, in addition, for confirmation, the compounds represented by the above-described formula [12] correspond to ones that Ar in the above-described general formula [1] is an anthraquinonyl group represented by the above-described general formula [III], all of $R^{14}$ to $R^{20}$ in the general formula [II] are a hydrogen atom, $R^1$ and $R^2$ are ones which form an alicyclic ring containing a nitrogen atom together with a nitrogen atom to which these ($R^1$ and $R^2$) are bound, which the ring have 5 carbon atoms, wherein a substituent is not contained, and also, no hetero atom other than a nitrogen atom is contained in the chain, and a hydrogen atom bound to a carbon atom constituting an alicyclic ring is not substituted by a methyl group i.e. a piperidine ring, and $R^3$ is a hydrogen atom, and $R^4$ is an alkyl group having 1 carbon atom, i.e. a methyl group.

Furthermore, more preferable examples of the compound represented by the above-described general formula [4] include ones that Ar' in the general formula [4] is an anthracenyl group represented by the above-described formula [IV], $R^{2\prime}$ is a linear alkyl group having 3 carbon atoms or a cyclic alkyl group having 6 carbon atoms, and $R^{3\prime}$ and $R^{4\prime}$ are both a hydrogen atom, more specifically, the compound represented by the formula [14]:

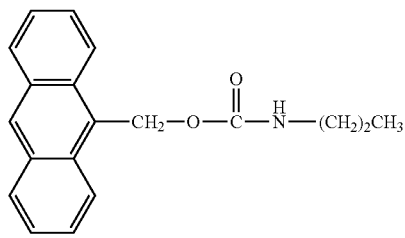

[14]

and the compound represented by the formula [15]:

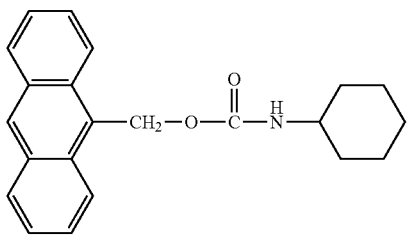

[15]

are more preferably exemplified.

Further, in addition, for confirmation, the compounds represented by the above-described formula [14] and [15] correspond to ones that Ar in the above-described general formula [1] is an anthracenyl group represented by the above-described general formula [I], all of $R^5$ to $R^{13}$ in the general formula [I] are a hydrogen atom, $R^1$ is a hydrogen atom, $R^2$ is a linear alkyl group having 3 carbon atoms, i.e. a n-propyl group or a cyclic alkyl group having 6 carbon atoms, i.e. a cyclohexyl group, and $R^3$ and $R^4$ are both a hydrogen atom.

Furthermore, more preferable examples of the compound represented by the above-described general formula [5] include ones that Ar' in the general formula [5] is an anthracenyl group represented by the above-described formula [IV], and $R^{3\prime}$ and $R^{4\prime}$ are both a hydrogen atom, and $R^{30}$ is a hydroxyl group, more specifically, the compound represented by the formula [16] are more preferably exemplified.

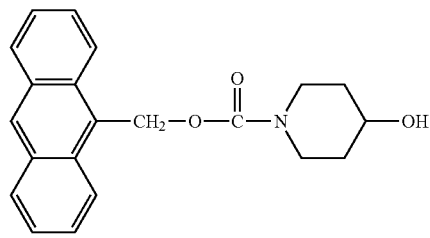

[16]

Further, in addition, for confirmation, the compounds represented by the above-described formula [16] correspond to ones that Ar in the above-described general formula [1] is an anthracenyl group represented by the above-described general formula [I], all of $R^5$ to $R^{13}$ in the general formula [I] are a hydrogen atom, $R^1$ and $R^2$ are ones which form an alicyclic ring containing a nitrogen atom together with a nitrogen atom to which they ($R^1$ and $R^2$) are bound, which the ring has 5 carbon atoms, wherein a hydroxyl group is contained as a substituent, and also, no hetero atom other than a nitrogen atom is contained in the chain, and a hydrogen atom bound to a carbon atom constituting an alicyclic ring is not substituted by a methyl group i.e. a 4-hydroxypiperidine ring, and $R^3$ and $R^4$ are both a hydrogen atom.

When the compound represented by the above-described general formula [1] is used as a photobase generator, for example, the photobase generator represented by the formula [9] that Ar' in the above-described general formula [2] is an anthracenyl group represented by the above-described formula [IV], $R^{3\prime}$ and $R^{4\prime}$ are both a hydrogen atom, and p and q are both 7,

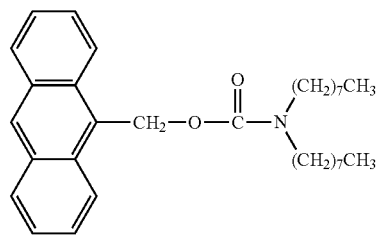

[9]

for example, the photobase generator represented by the formula [6]:

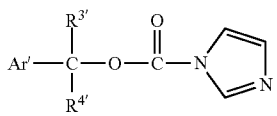

[6]

(wherein Ar', $R^{3\prime}$ and $R^{4\prime}$ are the same as above) that $R^5$ to $R^{29}$ in the above-described general formula [I] to [III] represented by Ar in the above-described general formula [1] are each independently a hydrogen atom or a halogen atom, $R^1$ and $R^2$ are ones which form an aromatic ring containing nitrogen atoms together with a nitrogen atom to which they ($R^1$ and $R^2$) are bound, which the ring has 3 carbon atoms, wherein a substituent is not contained, and also, a hydrogen atom bound to a carbon atom constituting an aromatic ring is not substituted by a methyl group or an ethyl group, and $R^3$ and $R^4$ are each independently a hydrogen atom or a linear alkyl group having 1 to 3 carbon atoms, may be preferable.

Further, in addition, for confirmation, the photobase generator represented by the above-described formula [9] correspond to ones that Ar in the above-described general formula [1] is an anthracenyl group represented by the above-described general formula [I], all of $R^5$ to $R^{13}$ in the general formula [I] are a hydrogen atom, $R^1$ and $R^2$ are both an alkyl group having 8 carbon atoms, i.e. a n-octyl group, and $R^3$ and $R^4$ are both a hydrogen atom.

Also, more preferable examples of the photobase generator represented by the above-described general formula [6] include ones that Ar' in the general formula [6] is an anthracenyl group represented by the above-described formula [IV], and $R^{3'}$ and $R^{4'}$ are both a hydrogen atom, more specifically, the photobase generator represented by the formula [17] is more preferably exemplified.

[17]

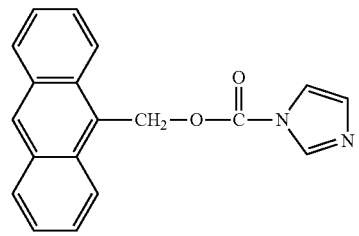

Further, in addition, for confirmation, the photobase generator represented by the above-described formula [17] correspond to ones that Ar in the above-described general formula [1] is an anthracenyl group represented by the above-described general formula [I], all of $R^5$ to $R^{13}$ in the general formula [I] are a hydrogen atom, $R^1$ and $R^2$ are ones which form an aromatic ring containing nitrogen atoms together with a nitrogen atom to which these ($R^1$ and $R^2$) are bound, which the ring has 3 carbon atoms, wherein a substituent is not contained, and also, an hydrogen atom bound to a carbon atom constituting an aromatic ring is not substituted by a methyl group or an ethyl group i.e. an imidazole ring, and $R^3$ and $R^4$ are both a hydrogen atom.

In addition, the compounds represented by the above-described general formula [1] other than the above-described specific compounds are exemplified as ones represented by the following chemical formula, however, shall not be limited thereto.

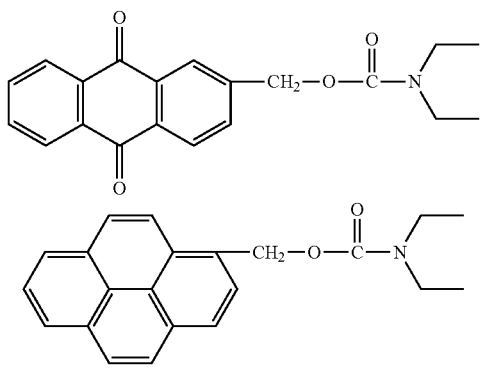

-continued

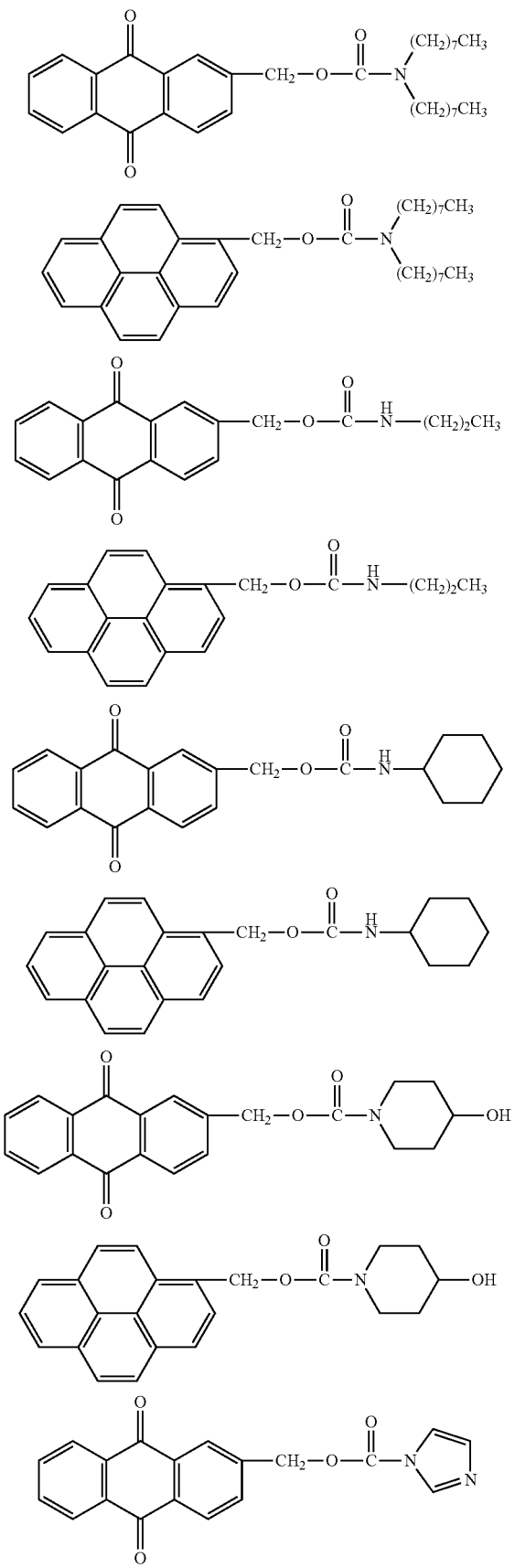

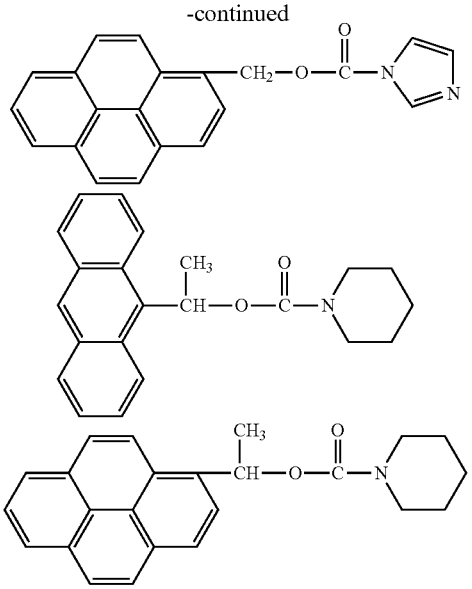

The compounds of the present invention generate a base when irradiated with 200 nm or longer wavelength light (active energy rays), more specifically 200 nm to 500 nm wavelength light (active energy rays), for example, generation of base by using 254 nm wavelength light (active energy rays) and the like which irradiate for the conventional photobase generator is not excluded, however, as described above, it is characterized that the compounds of the present invention can generate the base by irradiated with light (active energy rays) to which the conventional photobase generator is exposed, as well as irradiated with longer wavelength light (active energy rays) comparing with these wavelength lights, more specifically, for example, even when irradiated with 300 nm or longer wavelength light (active energy rays) such as 365 nm wavelength light (active energy rays), the compounds can efficiently generate the base. In addition, more preferable range of the above-described light (active energy rays) is 300 nm to 500 nm wavelength light (active energy rays), in these preferable ranges, the compounds of the present invention exhibit excellent sensitivity, more specifically, in the above-described range of 300 nm to 500 nm, the compounds of the present invention can efficiently generate the base because the absorption wavelength ranges in which molar absorption coefficient exhibits 3000 or more in these compounds exist.

As mentioned above, though it was described that the compounds of the present invention can generate a base when irradiated with light (active energy rays), the compounds of the present invention include the compounds which can generate the base by adding heat. Therefore, such compounds may generate the base by adding heat. That is, the compounds of the present invention include not only the photobase generator but the compounds that can become a heat-base generator, i.e. in the compounds of the present invention include ones which can be used in the base generation method in which can generate the base by irradiation of light (active energy rays) or/and addition of heat.

Subsequently, the production method of the compounds of the present invention is described in detail. As the production method of the compounds represented by the general formula [1] of the present invention, for example, the alcohol represented by the general formula [18]:

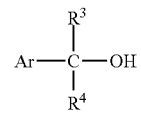

[18]

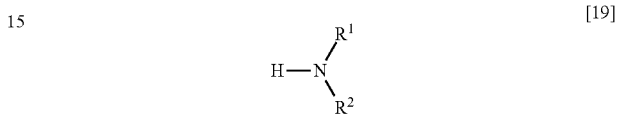

(wherein, Ar, $R^3$ and $R^4$ are the same as above), and a halogenated formic acid ester or N,N'-carbonyldiimidazole are reacted, when necessary, in the presence of an organic solvent, then an amine represented by the general formula [19]:

[19]

$$H-N\diagdown_{R^2}^{R^1}$$

(wherein, $R^1$ and $R^2$ are the same as above) can be reacted. As more specific production method, for example, the alcohol represented by the above-described general formula [18] and usually 0.8 to 10 equivalents, preferably 0.8 to 3 equivalents of the halogenated formic acid ester based on the above-described alcohol, for example, such as 4-nitrophenyl chloroformate are reacted in the presence of usually 0.8 to 20 equivalents, preferably 0.8 to 7 equivalents of a base based on the above-described alcohol, for example, such as triethylamine, when necessary, in the organic solvent such as dimethylacetamide (DMAc), or the alcohol represented by the above-described general formula [18] and usually 0.8 to 10 equivalents, preferably 0.8 to 3 equivalents of N,N'-carbonyldiimidazole based on the above-described alcohol are reacted, when necessary, in the organic solvent such as dimethylformamide (DMF) to obtain the correspondent carbonic acid ester (carbonate) or the urethane (carbamate) (First process). Then, the resultant carbonic acid ester (carbonate) or the urethane (carbamate) and usually 0.8 to 10 equivalents, preferably 0.8 to 3 equivalents of the amine represented by the above-described general formula [19] based on the above-described carbonic acid ester (carbonate) or the urethane (carbamate) are reacted, when necessary, in the organic solvent such as dichloromethane, dimethylformamide (DMF) to obtain the compound of the present invention represented by the general formula [1].

As the alcohols represented by the general formula [18] used in the above-described first process, commercially available products, or products synthesized by the conventional method may be appropriately used, and specifically, it includes, for example, 9-anthracenemethanol, 2-methylanthracene-9-methanol, 10-methylanthracene-9-methanol, 2-chloroanthracene-9-methanol, 2-bromoanthracene-9-methanol, 10-chloroanthracene-9-methanol, 10-bromoanthracene-9-methanol, 2,3-dimethylanthracene-9-methanol, 9-anthracene-1'-ethanol, 9-anthracene-1'-methyl-1'-ethanol, 2-hydroxymethylanthraquinone, 1-methyl-2-hydroxymethylanthraquinone, 1-chloro-2-hydroxymethylanthraquinone, 1-bromo-2-hydroxymethylanthraquinone, 1,4-dimethyl-2-hydroxymethylanthraquinone, 1,5-dichloro-2-hydroxymethylanthraquinone, 1,5-dibromo-2-hydroxymethylanthraquinone, 2-(1 hydroxyethyl)anthraquinone, 2-(1'-methyl-1'-hydroxyethyl)anthraquinone, 1-pyrenemethanol, 1-pyrene-1'-ethanol, 1-pyrene-1'-methyl-1'-ethanol and the like, and any of the above-described alcohols may be used by selecting appropriately, dependent on the structure of the intended compound represented by the general formula [1], particularly, from the viewpoint that the intended compound represented by the general formula [1] can be inexpensively, easily produced and the like, 9-anthracenemethanol, 10-bromoanthracene-9-methanol, 2-hydroxymethylanthraquinone, 2-(1'-hydroxyethyl)anthraquinone, 1-pyrenemethanol are preferable.

The halogenated formic acid esters used in the reaction to obtain the carbonic acid ester (carbonate) in the above-described first process include, specifically, for example, alkyl halogenated formate such as methyl chloroformate, methyl bromoformate, ethyl chloroformate, ethyl bromoformate, propyl chloroformate, propyl bromoformate, butyl chloroformate, butyl bromoformate; for example, aryl halogenated formate such as phenyl chloroformate, phenyl bromoformate, 2-chlorophenyl chloroformate, 2-chlorophenyl bromoformate, 4-chlorophenyl chloroformate, 4-chlorophenyl bromoformate, 2-bromophenyl chloroformate, 2-bromophenyl bromoformate, 4-bromophenyl chloroformate, 4-bromophenyl bromoformate, 2-nitrophenyl chloroformate, 2-nitrophenyl bromoformate, 4-nitrophenyl chloroformate, 4-nitrophenyl bromoformate, naphthyl chloroformate, naphthyl bromoformate; among them, for example, phenyl chloroformate, phenyl bromoformate, 2-chlorophenyl chloroformate, 2-chlorophenyl bromoformate, 4-chlorophenyl chloroformate, 4-chlorophenyl bromoformate, 2-bromophenyl chloroformate, 2-bromophenyl bromoformate, 4-bromophenyl chloroformate, 4-bromophenyl bromoformate, 2-nitrophenyl chloroformate, 2-nitrophenyl bromoformate, 4-nitrophenyl chloroformate, 4-nitrophenyl bromoformate, naphthyl chloroformate, naphthyl bromoformate are preferable; among them, 2-nitrophenyl chloroformate, 2-nitrophenyl bromoformate, 4-nitrophenyl chloroformate, 4-nitrophenyl bromoformate are more preferable; further among them, 4-nitrophenyl chloroformate, 4-nitrophenyl bromoformate are particularly preferable. By using aryl halogenated formate, in the second process using the carbonic acid ester (carbonate) obtained here as raw material, the reaction with the amine represented by the general formula [19] can selectively proceed to obtain the intended compound represented by the general formula [1] in high yield, and thus it is preferable. In addition, when the electron-attracting group such as 4-nitrophenyl chloroformate substituted aryl halogenated formate is used, in the second process, the reaction can more selectively proceed to obtain the intended compound represented by the general formula [1] in higher yield, and therefore it is more preferable. These halogenated formic acid esters may be used alone or in combination of 2 or more kinds. It should be noted that, these halogenated formic acid esters may be sufficient for use of the commercially available products.

It should be noted that, when usage of the above-described halogenated formic acid esters is less than 0.8 equivalents, reaction yield of the carbonic acid ester (carbonate) obtained by this reaction, reduces, on the other hand, when amount of more than 10 equivalents of the halogenated formic acid esters is used, there is occurred problems that it is economically inefficient and the like, therefore it is undesirable.

As the bases used in the reaction to obtain the carbonic acid ester (carbonate) in the above-described first process, any of tertiary amines which is usually used in this field may be used, specifically, it includes, for example, chained tertiary amines such as triethylamine, tri-n-propylamine, triisopropylamine, tri-n-butylamine, triisobutylamine, tri-n-pentylamine, triisopentylamine, N,N-diethylmethylamine, N,N-diisopropylmethylamine, N,N-diisopropylethylamine, N,N-di-n-butylmethylamine, N,N-diisobutylmethylamine, N,N-dimethyl-n-pentylamine, N,N-dimethylcyclopentylamine, N,N-dimethyl-n-hexylamine, N,N-dimethylcyclohexylamine, N,N-dimethylbenzylamine; for example, cyclic tertiary amines such as oxazole, thiazole, pyridine, N,N-dimethyl-4-aminopyridine, pyrazine, and the like. These amines may be used alone or in combination of 2 or more kinds, and as usage of the base, it is preferable to use more amount of the base than usage of the halogenated formic acid ester used in this reaction in order to trap hydrogen halide(s) formed from this reaction sufficiently.

The organic solvents which can be used, when necessary, in the reaction to obtain the carbonic acid ester (carbonate) in the above-described first process include, for example, non-polar organic solvents such as hexane, benzene, toluene, dichloromethane, chloroform, diethylether, tetrahydrofuran (THF), ethyl acetate; for example, aprotic polar solvents such as acetone, acetonitrile, dioxane, dimethylformamide (DMF), dimethylacetamide (DMAc), dimethylsulfoxide (DMSO), among them, so-called dehydrated organic solvents from which the organic solvents are dehydrated are preferable. More specifically, for example, dehydrated non-polar organic solvents such as dehydrated hexane, dehydrated benzene, dehydrated toluene, dehydrated dichloromethane, dehydrated chloroform, dehydrated diethylether, dehydrated tetrahydrofuran (dehydrated THF), dehydrated ethyl acetate; for example, dehydrated aprotic polar organic solvents such as dehydrated acetone, dehydrated acetonitrile, dehydrated dioxane, dehydrated dimethylformamide (dehydrated DMF), dehydrated dimethylacetamide (dehydrated DMAc), dehydrated dimethylsulfoxide (dehydrated DMSO); among them, for example, dehydrated aprotic polar organic solvents such as dehydrated acetone, dehydrated acetonitrile, dehydrated dioxane, dehydrated dimethylformamide (dehydrated DMF), dehydrated dimethylacetamide (dehydrated DMAc), dehydrated dimethylsulfoxide (dehydrated DMSO) are preferable, among them, dehydrated dimethylformamide (dehydrated DMF), dehydrated dimethylacetamide (dehydrated DMAc) are more preferable. These organic solvents may be used alone, or in combination of 2 or more kinds, and usage of the organic solvents is not particularly limited and is, for example, usually 0.5 to 30 mL, preferably 1 mL to 15 mL based on 1 mmol of the alcohol represented by the general formula [18].

Reaction temperature in the reaction to obtain the carbonic acid ester (carbonate) in the above-described first process may be set-up to the temperature at which the alcohol represented by the general formula [18] and the halogenated formic acid ester can be reacted, it is preferable to set-up the temperature at which the alcohol and the halogenated formic acid ester can be efficiently reacted to synthesize the carbonic acid ester (carbonate) with good yield. Specifically, for example, it is usually −20° C. to 100° C., preferably 0° C. to 60° C. In addition, the above-described reaction is exothermic; therefore, it is preferable that the alcohol and the halogenated formic acid ester are reacted on the condition that too high reaction temperature is avoided.

Reaction time in the reaction to obtain the carbonic acid ester (carbonate) in the above-described first process may be varied due to usage of the halogenated formic acid ester based on the alcohol represented by the general formula [18], presence or absence of the organic solvent, kinds and usage thereof, reaction temperature and the like, therefore, it cannot be unconditionally described, it is usually set-up in the range of 0.5 to 72 hours, preferably 1 to 48 hours.

Isolation, purification method of the carbonic acid ester (carbonate) which is the main product of the first process, from the solution after completing reaction in the reaction of the above-described first process to obtain the carbonic acid ester (carbonate) may be the general post-treatment, purification operation. Specifically, for example, it can be efficiently purified by a method that ice-water is added into the solution after completing the reaction, then, the solution is extracted with the appropriate solvent, after the extract is condensed, a solvent such as water is added into the condensate, and so the resultant crystal is filtered, then, is washed with the appropriate an organic solvent. It should be noted that, even when it is not the above-described purification operation, purification operation by the usual recrystallization or column chromatography may be employed, also, the second process may be carried out without isolating and purifying the carbonic acid ester (carbonate) from the reaction solution.

When usage of the N,N'-carbonyldiimidazole used in the reaction to obtain the urethane (carbamate) in the above-described first process is less than 0.8 equivalents, yield of the urethane (carbamate) obtained by this reaction, reduces, on the other hand, when amount of more than 10 equivalents of the N,N'-carbonyldiimidazole is used, there is occurred problems that it is economically inefficient and the like, therefore it is undesirable. It should be noted that, the N,N'-carbonyldiimidazole may be sufficient for use of the commercially available products.

The organic solvents which can be used, when necessary, in the reaction to obtain the urethane (carbamate) in the above-described first process include, for example, non-polar organic solvents such as tetrahydrofuran (THF); for example, aprotic polar organic solvents such as acetone, methylethylketone, methylisobutylketone, acetonitrile, dimethylformamide (DMF), dimethylacetamide (DMAc), dimethylsulfoxide (DMSO); among them, dimethylformamide (DMF) are preferable. These organic solvents may be used alone or in combination of 2 or more kinds, and usage of the organic solvents is not particularly limited and is, for example, usually 0.2 mL to 20 mL, preferably 0.5 mL to 10 mL based on 1 mmol of the alcohol represented by the general formula [18].

Reaction temperature in the reaction of the above-described first process to obtain the urethane (carbamate) may be set-up to the temperature at which the alcohol represented by the general formula [18] and the N,N'-carbonyldiimidazole can be reacted, it is preferable to set-up the temperature at which the alcohol and the N,N'-carbonyldiimidazole can be efficiently reacted to synthesize the urethane (carbamate) with good yield. Specifically, for example, it is usually −30° C. to 80° C., preferably −10° C. to 40° C.

Reaction time in the reaction of the above-described first process to obtain the urethane (carbamate) may be varied due to usage of the N,N'-carbonyldiimidazole based on the alcohol represented by the general formula [18], presence or absence of the organic solvent, kinds and usage thereof, reaction temperature and the like, therefore, it cannot be unconditionally described, it is usually set-up in the range of 0.1 to 12 hours, preferably 0.2 to 6 hours.

Isolation, purification method of the urethane (carbamate) which is the main product of the first process, from the solution after completing the reaction in the reaction of the above-described first process to obtain the urethane (carbamate) may be the general post-treatment, purification operation. Specifically, for example, it can be efficiently purified by a method that the solution after completing the reaction is added into water, then, the resultant crystal is filtered, and is washed with the appropriate an organic solvent. It should be noted that, even when it is not the above-described purification operation, purification operation by the usual recrystallization or column chromatography may be employed, also, the second process may be carried out without isolating and purifying the urethane (carbamate) from the reaction solution.

As the amines represented by the general formula [19] used in the above-described second process, commercially available products or products synthesized by the conventional method may be appropriately used, and specifically, it includes, for example, ammonia, for example, linear, branched or cyclic mono or dialkylamines having 1 to 1.0 carbon atoms such as mono or dimethylamine, mono or diethylamine, mono or di-n-propylamine, mono or diisopropylamine, mono or di-n-butylamine, mono or diisobutylamine, mono or di-sec-butylamine, mono or di-tert-butylamine, mono or dicyclobutylamine, mono or di-n-pentylamine, mono or diisopentylamine, mono or di-sec-pentylamine, mono or di-tert-pentylamine, mono or dineopentylamine, mono or di-2-methylbutylamine, mono or di-1,2-dimethylpropylamine, mono or di-1-ethylpropylamine, mono or dicyclopentylamine, mono or di-n-hexylamine, mono or diisohexylamine, mono or di-sec-hexylamine, mono or di-tert-hexylamine, mono or dineohexylamine, mono or di-2-methylpentylamine, mono or di-1,2-dimethylbutylamine, mono or di-2,3-dimethylbutylamine, mono or di-1-ethylbutylamine, mono or dicyclohexylamine, mono or di-n-heptylamine, mono or diisoheptylamine, mono or di-sec-heptylamine, mono or di-tert-heptylamine, mono or dineoheptylamine, mono or dicycloheptylamine, mono or di-n-octylamine, mono or diisooctylamine, mono or di-sec-octylamine, mono or di-tert-octylamine, mono or dineooctylamine, mono or di-2-ethylhexylamine, mono or dicyclooctylamine, mono or di-n-nonylamine, mono or diisononylamine, mono or di-sec-nonylamine, mono or di-tert-nonylamine, mono or dineononylamine, mono or dicyclononylamine, mono or di-n-decylamine, mono or diisodecylamine, mono or di-sec-decylamine, mono or di-tert-decylamine, mono or dineodecylamine, mono or dicyclodecylamine, mono or dinorbornylamine, mono or diadamantylamine, ethylmethylamine, methyl-n-propylamine, methylisopropylamine, ethyl-n-propylamine, ethylisopropylamine, n-propylisopropylamine; for example, alicyclic amines having 3 to 8 carbon atoms such as azetidine, pyrrolidine, 2,5-dimethylpyrrolidine, piperidine, 2,6-dimethylpiperidine, 2,4,6-trimethylpiperidine, hexamethyleneimine, heptamethyleneimine, octamethyleneimine, oxazolidine, thiazolidine, morpholine, 2,3,5,6-tetramethylmorpholine, thiomorpholine, 2,3,5,6-tetramethylthiomorpholine; for example, alicyclic amines having 3 to 8 carbon atoms and having a substituent (a functional group) other than hydrocarbon groups such as 4-hydroxypiperidine, 4-mercaptopiperidine, 4-cyanopiperidine, 4-nitropiperidine, 4-chloropiperidine, 4-bromopiperidine; for example, aromatic amines having 3 to 8 carbon atoms such as pyrrole, imidazole, pyrazole, 2,5-dimethylpyrrole, 2,5-diethylpyrrole, 2,5-dimethylimidazole, 2,5-diethylimidazole, 3,5-dimethylpyrazole, 3,5-diethylpyrazole, and the like, and any of the above-described amines may be used by selecting appropriately, particularly, from the viewpoint that the amines are easily available, and the intended compounds represented by the general formula [1] can become the photobase generator which can more efficiently generate base; and preferable amines are linear or cyclic monoalkylamines having 3 to 8 carbon atoms such as mono-n-propylamine, mono-n-butylamine, monocyclobutylamine, mono-n-pentylamine, monocyclopentylamine, mono-n-hexylamine, monocyclohexylamine, mono-n-heptylamine, monocycloheptylamine, mono-n-octylamine, monocyclooctylamine; for example, linear dialkylamines having 1 to 8 carbon atoms such as dimethylamine, diethylamine, di-n-propylamine, di-n-butylamine, di-n-pentylamine, di-n-hexylamine, di-n-heptylamine, di-n-octylamine; for example, alicyclic amines having 4 to 7 carbon atoms, wherein a substituent is not contained, and also no hetero atom other than a nitrogen atom is contained in the chain, and a hydrogen atom bound to a carbon atom constituting an alicyclic ring is not substituted by a methyl group such as pyrrolidine, piperidine, hexamethyleneimine, heptamethyleneimine; for example, alicyclic amines having 5 carbon atoms, wherein a substituent is contained, and also no hetero atom other than a nitrogen atom is contained in the chain, and a hydrogen atom bound to a carbon atom constituting an alicyclic ring is not substituted by a methyl group such as 4-hydroxypiperidine, 4-mercaptopiperidine, 4-cyanopiperidine, 4-nitropiperidine, 4-chloropiperidine, 4-bromopiperidine; for example, aromatic amines having 3 to 4 carbon atoms, wherein a substituent is not contained, and also a hydrogen atom bound to a carbon atom constituting an aromatic ring is not substituted by a methyl group or an ethyl group such as pyrrole, imdazole, pyrazole.

It should be noted that, when usage of the amines represented by the above-described general formula [19] is less than 0.8 equivalents, the reaction yield of the compounds represented by the general formula [1] obtained by this reaction, reduces, on the other hand, when amount of more than 10 equivalents of the amines is used, there is occurred problems that the yield of the intended compounds represented by the general formula [1] reduces, because 2 molecules of the amine are reacted based on 1 molecule of the carbonic acid ester (carbonate) or the urethane (carbamate), and it is economically inefficient and the like, therefore it is undesirable.

As the organic solvents which can be used, when necessary, in the above-described second process, there are not particularly limited, so long as there are organic solvents which do not react with the carbonic acid ester (carbonate) or the urethane (carbamate) of the reaction raw materials and the compounds represented by the general formula [1], specifically, it includes, for example, non-polar organic solvents such as hexane, benzene, toluene, dichloromethane, chloroform, diethylether, tetrahydrofuran (THF), ethyl acetate; for example, aprotic polar organic solvents such as acetone, acetonitrile, dioxane, dimethylformamide (DMF), dimethylacetamide (DMAc), dimethylsulfoxide (DMSO) and the like, in addition, the dehydrated organic solvents preferably used in the reaction to obtain the urethane (carbamate) in the first process, such as the dehydrated dimethylacetamide (dehydrated DMAc) may be used. These organic solvents may be used alone or in combination of 2 or more kinds, and usage of the organic solvents is not particularly limited and is, for example, usually 0.2 mL to 300 mL, preferably 0.5 mL to 150 mL based on 1 mmol of the carbonic acid ester (carbonate) or the urethane (carbamate) obtained by the first process.

It should be noted that, in the reaction using the urethane (carbamate) in the above-described second process, in order to activate imidazole which functions as the leaving group, for example, an alkylating agent such as a methyl iodide, an ethyl iodide may be used. Usage of alkylating agents is sufficient for amount by which imidazole can be activated and specifically, is, for example, usually 0.8 to 10 equivalents, preferably 0.8 to 3 equivalents based on the urethane (carbamate) obtained by the first process.

Reaction temperature in the reaction of the above-described second process may be set-up to the temperature at which the carbonic acid ester (carbonate) or the urethane (carbamate) obtained by the first process and the amine represented by the general formula [19] can be reacted, it is preferable to set-up the temperature at which the carbonic acid ester (carbonate) or the urethane (carbamate) and the amine can be efficiently reacted to synthesize the compounds represented by the general formula [1] with good yield. Specifically, for example, it is usually −20° C. to 100° C., preferably 0° C. to 80° C.

Reaction time in the reaction of the above-described second process may be varied due to usage of the amine represented by the general formula [19] based on the carbonic acid ester (carbonate) or the urethane (carbamate) obtained by the first process, presence or absence of the organic solvent, kinds and usage thereof, reaction temperature and the like, therefore, it cannot be unconditionally described, it is usually set-up in the range of 0.1 to 24 hours, preferably 0.5 to 12 hours.

Isolation, purification method of the intended compounds represented by the general formula [1] from the solution after completing reaction in the reaction of above-described second process may be the general post-treatment, purification operation. Specifically, for example, the solution after completing the reaction is washed with water, and the solution after washing is condensed, then, the appropriate purification operation such as recrystallization, column chromatography and the like may be carried out to isolate, and water (ice-water) is added to the solution after completing the reaction, then, the resultant crystal is filtered, and may be washed with the appropriate organic solvent to isolate.

It should be noted that, as the alternative method by which the compounds represented by the general formula [1] of the present invention is produced, the reaction of the alcohol represented by the above-described general formula [18] and the compound represented by the general formula [20]:

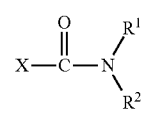

[20]

(wherein X represents a halogen atom, $R^1$ and $R^2$ are the same as above) can be exemplified. More specifically, for example, the compounds represented by the general formula [1] of the present invention can be obtained by reacting the alcohol represented by the above-described general formula [18], with usually 0.8 to 10 equivalents, preferably 0.8 to 3 equivalents of the compound represented by the general formula [20] based on the alcohol, when necessary, in the presence of usually 0.8 to 5 equivalents, preferably 0.8 to 3 equivalents of a base, for example, such as sodium hydride based on the above-described alcohol, when necessary, in an organic solvent such as dehydrated tetrahydrofuran (dehydrated THF), and the intended compound can be synthesized in one process by the method.

The halogen atoms represented by X in the general formula [20] include, specifically, for example, a chlorine atom, a bromine atom, an iodine atom and the like, among them, a chlorine atom, a bromine atom are preferable, among them, a chlorine atom is more preferable.

As described above, as the alcohols represented by the general formula [18] using in the above-described reaction, commercially available products or products synthesized by the conventional method may be appropriately used, and specifically, it includes, for example, 9-anthracenemethanol, 2-methylanthracene-9-methanol, 10-methylanthracene-9-methanol, 2-chloroanthracene-9-methanol, 2-bromoanthracene-9-methanol, 10-chloroanthracene-9-methanol, 10-bromoanthracene-9-methanol, 2,3-dimethylanthracene- 9-methanol, 9-anthracene-1'-ethanol, 9-anthracene-1'-methyl-1'-ethanol, 2-hydroxymethylanthraquinone, 1-methyl-2-hydroxymethylanthraquinone, 1-chloro-2-hydroxymethylanthraquinone, 1-bromo-2-hydroxymethylanthraquinone, 1,4-dimethyl-2-hydroxymethylanthraquinone, 1,5-dichloro-2-hydroxymethylanthraquinone, 1,5-dibromo-2-hydroxymethylanthraquinone, 2-(1'-hydroxyethyl) anthraquinone, 2-(1'-methyl-1'-hydroxyethyl) anthraquinone, 1-pyrenemethanol, 1-pyrene-1'-ethanol, 1-pyrene-1'-methyl-1'-ethanol and the like, and any of the above-described alcohols may be used by selecting appropriately, dependent on the structure of the intended compounds represented by the general formula [1], particularly, from the viewpoint that the intended compound represented by the general formula [1] can be inexpensively, easily produced and the like, 9-anthracenemethanol, 10-bromoanthracene-9-methanol, 2-hydroxymethylanthraquinone, 2-(1'-hydroxyethyl)anthraquinone, 1-pyrenemethanol are preferable.

The compounds represented by the general formula [20] used in the above-described reaction, may be sufficient for use of the commercially available products, specifically, for example, include the carbamoyl derivatives such as N,N-dialkylcarbamoyl halides such as N,N-dimethylcarbamoyl chloride, N,N-dimethylcarbamoyl bromide, N,N-diethylcarbamoyl chloride, N,N-diethylcarbamoyl bromide, N,N-di-n-propylcarbamoyl chloride, N,N-di-n-propylcarbamoyl bromide, N,N-diisopropylcarbamoyl chloride, N,N-diisopropylcarbamoyl bromide; for example, cyclic aminocarbonyl halides such as 1-pyrrolidinecarbonyl chloride, 1-pyrrolidinecarbonyl bromide, 2,5-dimethylpyrrolidine-1-carbonyl chloride, 2,5-dimethylpyrrolidine-1-carbonyl bromide, 1-piperidinecarbonyl chloride, 1-piperidinecarbonyl bromide, 2,6-dimethylpiperidine-1-carbonyl chloride, 2,6-dimethylpiperidine-1-carbonyl bromide, 4-morpholinecarbonyl chloride, 4-morpholinecarbonyl bromide, and the like, and any of the above-described carbamoyl derivatives may be used by selecting appropriately, dependent on the structure of the intended compound represented by the general formula [1], particularly, from the viewpoint that the carbamoyl derivatives are easily available, and the intended compounds represented by the general formula [1] can become the photobase generator which can more efficiently generate a base, N,N-diethylcarbamoyl chloride, N,N-diethylcarbamoyl bromide, 1-piperidinecarbonyl chloride, 1-piperidinecarbonyl bromide are preferable, among them, N,N-diethylcarbamoyl chloride, 1-piperidinecarbonyl chloride are more preferable.

It should be noted that, when usage of the compounds represented by the above-described general formula [20] is less than 0.8 equivalents, the reaction yield of the compounds represented by the general formula [1] obtained by this reaction, reduces, on the other hand, when amount of more than 10 equivalents of the compounds represented by the above-described general formula [20] is used, there is occurred problems that it is economically inefficient and the like, therefore it is undesirable.

As the bases, when necessary, used in the above-described reaction, specifically, it includes, for example, alkali metal hydrides such as sodium hydride, potassium hydride; for example, alkali metal hydroxides such as sodium hydroxide, potassium hydroxide; for example, carbonic acid alkali metal salts such as sodium carbonate, potassium carbonate, cesium carbonate; for example, alkali metal alkoxides such as sodium methoxide, potassium methoxide, sodium ethoxide, potassium ethoxide, lithium tert-butoxide, sodium tert-butoxide, potassium tert-butoxide; for example, alkyllithium such as n-butyllithium, sec-butyllithium, tert-butyllithium, n-hexyllithium; for example, metal amides such as lithium diisopropylamide (LDA), lithium hexamethyldisilazane (LHMDS), sodium hexamethyldisilazane (NaHMDS), potassium, hexamethyldisilazane (KHMDS); for example, tertiary amines such as triethylamine, pyridine, 1,8-diazabicyclo[5.4.0]undec-7-ene (DBU), 1,5-diazabicyclo[4.3.0]non-5-ene (DBN), and the like, among them, alkali metal hydrides such as sodium hydride, potassium hydride are preferable, among them, sodium hydride is more preferable. These bases may be used alone or in combination of 2 or more kinds, and as usage of the bases, it is preferable to use more amount of the bases than usage of the alcohol used in this reaction in order to progress the deprotonation reaction of the alcohol represented by the general formula [18] smoothly.

It should be noted that, as bases, when necessary, used in the above-described reaction, when the base containing alkali metal(s) such as alkali metal hydrides such as sodium hydride, potassium hydride is used, in order to accelerate the deprotonation reaction of the alcohol represented by the general formula [18], crown ethers such as 12-crown-4-ether, 15-crown-5-ether, 18-crown-6-ether may be used for the purpose of complementing the counter cation of the base. Usage of these crown ethers is not particularly limited, and it may be used in arbitrary ratio based on usage of the above-described base, this usage may be appropriately controlled.

In addition, the activating agents such as N,N-dimethyl-4-aminopyridine may be used in order to activate the compound represented by the general formula [20] in the above-described reaction. Usage of these activating agents is not particularly limited, its usage is sufficient by catalytic amount, for example, usually 0.001 to 0.5 mmol, preferably 0.001 to 0.2 mmol based on 1 mmol of the alcohol represented by the general formula [18].

The organic solvents, when necessary, used in the above-described reaction, which do not react with the alcohol represented by the general formula [18] of the reaction raw materials and the compound represented by the general formula [20], are not particularly limited, specifically, include, for example, non-polar organic solvents such as hexane, benzene, toluene, diethylether, tetrahydrofuran (THF); for example, aprotic polar organic solvents such as acetonitrile, dioxane, dimethylformamide (DMF), dimethylacetamide (DMAc), dimethylsulfoxide (DMSO); for example, dehydrated non-polar organic solvents, from which these organic solvents are dehydrated, such as dehydrated hexane, dehydrated benzene, dehydrated toluene, dehydrated diethylether, dehydrated tetrahydrofuran (dehydrated THF); for example, dehydrated aprotic polar organic solvents such as dehydrated acetonitrile, dehydrated dioxane, dehydrated dimethylformamide (dehydrated DMF), dehydrated dimethylacetamide (dehydrated DMAc), dehydrated dimethylsulfoxide (dehydrated DMSO), among them, dehydrated organic solvents for example, such as dehydrated non-polar organic solvents such as dehydrated hexane, dehydrated benzene, dehydrated toluene, dehydrated diethylether, dehydrated tetrahydrofuran (dehydrated THF); for example, dehydrated aprotic polar organic solvents such as dehydrated acetonitrile, dehydrated dioxane, dehydrated dimethylformamide (dehydrated DMF), dehydrated dimethylacetamide (dehydrated DMAc), dehydrated dimethylsulfoxide (dehydrated DMSO) are preferable, further among them, dehydrated diethylether, dehydrated tetrahydrofuran (dehydrated THF), dehydrated acetonitrile are more preferable. When the dehydrated organic solvents are used in the reaction, side reaction between trace of water having in the organic solvents and bases, for example, such as sodium hydride can be suppressed, and deprotonation reaction of the alcohol represented by the general formula [18] by the base can be efficiently carried out, therefore, it is preferable to use the dehydrated organic solvents for the reaction. In addition, these organic solvents may be used alone or in combination of 2 or more kinds, usage of the organic solvents is not particularly limited, for example, is usually 0.5 mL to 30 mL, preferably 0.8 mL to 15 mL based on 1 mmol of the alcohol represented by the general formula [18].

Reaction temperature in the above-described reaction may be set-up to the temperature at which the alcohol represented by the general formula [18] and the compound represented by the general formula [20] can be reacted, and it is preferable to set-up the temperature at which the alcohol and the compound represented by the general formula [20] can be efficiently reacted to synthesize the compounds represented by the general formula [1] with good yield. Specifically, for example, it is usually 0° C. to 120° C., preferably 20° C. to 100° C.

Reaction time in the above-described reaction may be varied due to usage of the compound represented by the general formula [20] based on the alcohol represented by the general formula [18], presence or absence of the base, kinds and usage thereof, presence or absence of the activating agent and the like, kinds and usage thereof, presence or absence of the organic solvent, kinds and usage thereof, reaction temperature and the like, therefore, it cannot be unconditionally described, it is usually set-up in the range of 0.1 to 24 hours, preferably 0.5 to 12 hours.

Isolation, purification method of the intended compounds represented by the general formula [1] from the solution after completing the reaction in the above-described reaction may be the general post-treatment, purification operation. Specifically, for example, the solution after completing the reaction is washed with water, and the solution after washing is condensed, then, the appropriate purification operation such as recrystallization, column chromatography and the like may be carried out to isolate, and water (ice-water) is added to the solution after completing the reaction, then, the resultant crystal is filtered, and may be washed with the appropriate organic solvent to isolate.

Hitherto, the method of producing the compound of the present invention has been described, however, the above-described method is only one example, and the compound of the present invention may be produced by another method. Specifically, for example, when the compound, in which the group represented by Ar in the general formula [1] is an anthracenyl group, an anthraquinonyl group or a pyrenyl group substituted by a halogen atom and/or an alkyl group, is produced, the compound represented by the general formula [1], into which the intended above-described a substituent on the aromatic ring is introduced, may be produced by the method that halogenation reaction and/or alkylation reaction are carried out for the group (aryl group) represented by Ar after the above-described first process and second process. In addition, for example, when the compound, in which $R^3$ and/or $R^4$ in the general formula [1] are an alkyl group, is produced, the compound represented by the general formula [1], in which $R^3$ and/or $R^4$ are an alkyl group, may be produced by the method that alkylation reaction is carried out onto the carbon (on the carbon in benzyl position), on which $R^3$ and/or $R^4$ is bound, after the above-described first process and second process.

The compound represented by the general formula [1] of the present invention obtained in this method, as described above, is useful as the photobase generator for light-hardening of the light-hardening resin, for example, such as the episulfide resin (the episulfide compound) useful as resist materials in the production process of the semiconductor device, surface protection film or interlayer insulation film for the semiconductor device, insulation material for electronic parts and the like. Also, the compounds of the present invention can be used as the above-described these uses, other than these uses, as the photobase generator for light-hardening of the conventional light-hardening resin such as the epoxy resin in which insufficiency of light sensitivity to the photobase generator has been pointed out, that is, these compounds can also be used as supply source of base for hardening resin.

EXAMPLES

Hereinafter, the present invention will be specifically explained referring to Examples, but the present invention is not limited thereto by any means.

Synthetic Example 1

Synthesis of 9-anthrylmethyl 4'-nitrophenylcarbonate (First Process)

To the solution dissolved 5.0 g of 9-anthracenemethanol (24 mmol; produced by Wako Pure Chemical Industries, Ltd.) into 250 mL of the dehydrated dimethylacetamide (dehydrated DMAc), 7.3 g of triethylamine (72 mmol) was added. After 4.9 g of 4-nitrophenyl chloroformate (24 mmol; produced by Wako Pure Chemical Industries, Ltd.) was added to this solution, the solution was reacted by stirring for 24 hours at room temperature. After completing the reaction, ice-water was poured into the reaction solution, and this mixed solution was extracted with dichloromethane, and further after organic layer after extraction was washed with water, the organic layer was condensed. Subsequently, water was poured into the condensed residue, and after the resultant crystal was filtered, the resultant crystal was dried to obtain 4.8 g of 9-anthrylmethyl 4'-nitrophenylcarbonate (yield: 53%) as yellow crystal. Measurement results of $^1$H-NMR are shown as the follows:

$^1$H-NMR (400 MHz, CDCl$_3$) δ (ppm): 6.39 (2H, s, OCH$_2$), 7.36 (2H, d, J=9.3 Hz, ArH), 7.51-7.54 (2H, m, ArH), 7.60-7.65 (2H, m, ArH), 8.06 (2H, d, J=8.7 Hz, ArH), 8.24 (2H, d, J=9.3 Hz, ArH), 8.41 (2H, d, J=8.7 Hz, ArH), 8.57 (1H, s, ArH).

Example 1

Synthesis of 9-anthrylmethyl 1-piperidinecarboxylate (Second Process)

To the solution dissolved 4.8 g of 9-anthrylmethyl 4'-nitrophenylcarbonate (13 mmol) obtained by Synthetic Example 1 into 100 mL of dichloromethane, 1.4 g of piperidine (16 mmol) was added, then, the solution was reacted by stirring for 1 hour at the room temperature. After completing the reaction, reaction solution was washed with water, organic layer after washing was condensed. By purifying the resultant condensed residue with column chromatography (Filler: silica-gel (Wako-gel C-200; produced by Wako Pure Chemical Industries, Ltd.), Developing solvent: dichloromethane) 1.3 g of 9-anthrylmethyl 1-piperidinecarboxylate (yield: 32%) represented by the above-described formula [10] as pale yellow crystal was obtained. Measurement results of $^1$H-NMR and melting point are shown as the follows:

$^1$H-NMR (400 MHz, CDCl$_3$) δ (ppm): 1.39 (2H, br, CH$_2$), 1.53 (4H, br, 2×CH$_2$), 3.28 (2H, br, NCH$_2$), 3.46 (4H, br, NCH$_2$), 6.15 (2H, s, OCH$_2$), 7.49-7.59 (4H, m, ArH), 8.03 (2H, d, J=8.8 Hz, ArH), 8.41 (2H, d, J=8.8 Hz, ArH), 8.50 (1H, s, ArH);

Melting point: 130-132° C.

Synthetic Example 2

Synthesis of 2-anthraquinonylmethyl 4'-nitrophenylcarbonate (First Process)

To the solution dissolved 3.0 g of 2-hydroxymethylanthraquinone (12 mmol; produced by Tokyo Chemical Industry Co., Ltd.) into 100 mL of dehydrated dimethylacetamide (dehydrated DMAc), 3.8 g of triethylamine (37 mmol) was added. After 2.5 g of 4-nitrophenyl chloroformate (12 mmol; produced by Wako Pure Chemical Industries, Ltd.) was added to this solution, the solution was reacted by stirring for 24 hours at room temperature. After completing the reaction, ice-water was poured into the reaction solution, the resultant crystal was filtered, then, the resultant crystal was dried to obtain 2.4 g of 2-anthraquinonylmethyl 4'-nitrophenylcarbonate (yield: 47%) as pale yellow crystal. Measurement results of $^1$H-NMR are shown as the follows:

$^1$H-NMR (400 MHz, CDCl$_3$) δ (ppm): 5.47 (2H, s, OCH$_2$), 7.42 (2H, d, J=9.3 Hz, ArH), 7.82-7.85 (3H, m, ArH), 8.29-8.39 (4H, m, ArH), 8.30 (2H, d, J=9.3 Hz, ArH).

Example 2

Synthesis of 2-anthraquinonylmethyl 1-piperidinecarboxylate (Second Process)

To the solution dissolved 2.4 g of 2-anthraquinonylmethyl 4'-nitrophenylcarbonate (5.8 mmol) obtained by Synthetic Example 2 into 450 mL of dehydrated dimethylacetamide (dehydrated DMAc), 0.60 g of piperidine (7.0 mmol) was added, then, the solution was reacted by stirring for 1 hour at room temperature. After completing the reaction, ice-water was poured into the reaction solution, the resultant crystal was filtered, then, the resultant crystal was dried to obtain 1.1 g of 2-anthraquinonylmethyl 1-piperidinecarboxylate (yield: 55%) represented by the above-described formula [11] as pale yellow crystal. Measurement results of $^1$H-NMR and melting point are shown as the follows:

$^1$H-NMR (400 MHz, CDCl$_3$) δ (ppm): 1.55-1.63 (6H, m, 3×CH$_2$), 3.49 (4H, br, 2×NCH$_2$), 5.29 (2H, s, OCH$_2$), 7.76-7.83 (3H, m, ArH), 8.27-8.34 (4H, m, ArH);

Melting point: 146-147° C.

Synthetic Example 3

Synthesis of 1-pyrenylmethyl 4'-nitrophenylcarbonate (First Process)

To the solution dissolved 5.0 g of 1-pyrenemethanol (22 mmol; produced by Tokyo Chemical Industry Co., Ltd.) into 200 mL of dehydrated dimethylacetamide (dehydrated DMAc), 6.5 g of triethylamine (65 mmol) was added. After 4.3 g of 4-nitrophenyl chloroformate (22 mmol; produced by Wako Pure Chemical Industries, Ltd.) was added to this solution, the solution was reacted by stirring for 24 hours at room temperature. After completing the reaction, ice-water was poured into the reaction solution, and this mixed solution was extracted with dichloromethane, and further after organic layer after extraction was washed with water, the organic layer was condensed. Subsequently, toluene was poured into the condensed residue, and after the resultant crystal was filtered, the resultant crystal was dried to obtain 5.9 g of 1-pyrenylmethyl 4'-nitrophenylcarbonate (yield: 68%) as yellow crystal. Measurement results of $^1$H-NMR are shown as the follows:

$^1$H-NMR (400 MHz, CDCl$_3$) δ (ppm): 6.02 (2H, s, OCH$_2$), 7.25 (2H, d, J=9.3 Hz, ArH), 7.98-8.20 (9H, m, ArH), 8.27 (2H, d, J=9.3 Hz, ArH).

Example 3

Synthesis of 1-pyrenylmethyl 1-piperidinecarboxylate (Second Process)

To the solution dissolved 5.9 g of 1-pyrenylmethyl 4'-nitrophenylcarbonate (15 mmol) obtained by Synthetic Example 3 into 50 mL of dehydrated dimethylacetamide (dehydrated DMAc), 1.4 g of piperidine (16 mmol) was added, then, the solution was reacted by stirring for 2 hours at room temperature. After completing the reaction, ice-water was poured into the reaction solution, and this mixed solution was extracted with dichloromethane, and further after organic layer after extraction was washed with water, the organic layer was condensed. The resultant condensed residue was purified with column chromatography (Filler: Silica-gel (Wako-gel C-200; produced by Wako Pure Chemical Industries, Ltd.), Developing solvent: dichloromethane) to obtain 1.6 g of 1-pyrenylmethyl 1-piperidinecarboxylate (yield: 32%) represented by the above-described formula [13] as orange crystal. Measurement results of $^1$H-NMR and melting point are shown as the follows:

$^1$H-NMR (400 MHz, CDCl$_3$) δ (ppm): 1.54 (6H, br, 3×CH$_2$), 3.43 (4H, br, 2×NCH$_2$), 5.83 (2H, s, OCH$_2$), 7.99-8.34 (9H, m, ArH);

Melting point: 118-120° C.

Example 4

Synthesis of 9-anthrylmethyl N,N-diethylcarbamate

To the solution containing 1.6 g of 50% sodium hydrate (33 mmol) and 4 mL of dehydrated tetrahydrofuran (dehydrated THF), the solution dissolved 6.3 g of 9-anthracenemethanol (30 mmol; produced by Wako Pure Chemical Industries, Ltd.) into 26 mL of dehydrated tetrahydrofuran (dehydrated THF) was dropped. Then, after this solution of 4.5 g of N,N-diethylcarbamoyl chloride (33 mmol; produced by Sigma-Aldrich Japan Co.) in 4 mL of dehydrated tetrahydrofuran (dehydrated THF) was added, the solution was reacted by stirring for 2 hours at 60° C. After completing reaction, reaction solution was cooled, and n-hexane was poured into the cooled solution, then, the solution was washed with water, and organic layer after washing was condensed. The resultant condensed residue was purified with column chromatography (Filler: Silica-Gel (Wako-Gel C-200; produced by Wako Pure Chemical Industries, Ltd.), Developing solvent: n-heptane) to obtain 5.7 g of 9-anthrylmethyl N,N-diethylcarbamate (yield: 61%) represented by the above-described formula [7] as yellow crystal. Measurement results of $^1$H-NMR and melting point are shown as the follows:

$^1$H-NMR (400 MHz, CDCl$_3$) δ (ppm): 0.91 (3H, br, CH$_3$), 1.14 (3H, br, CH$_3$), 3.14 (2H, br, NCH$_2$), 3.35 (2H, br, NCH$_2$), 6.14 (2H, s, OCH$_2$), 7.48 (2H, dd, J=8.0, 6.8 Hz, ArH), 7.57 (2H, dd, J=8.4, 6.8 Hz, ArH), 8.04 (2H, d, J=8.0 Hz, ArH), 8.46 (2H, d, J=8.4 Hz, ArH), 8.52 (1H, s, ArH);

Melting point: 72-74° C.

Example 5

Synthesis of 9-anthrylmethyl N-n-propylcarbamate (First and Second Process)

To the solution dissolved 8.92 g of N,N'-carbonyldiimidazole (55 mmol; produced by Wako Pure Chemical Industries, Ltd.) into 40 mL of dimethylformamide (DMF), 10.4 g of 9-anthracenemethanol (50 mmol; produced by Wako Pure Chemical Industries, Ltd.) was added under cooling with ice, then, the solution was reacted by stirring for 1 hour at the same temperature. Subsequently, 4.13 g of mono-n-propylamine (70 mmol; produced by Wako Pure Chemical Industries, Ltd.) was added to this solution, and the solution was reacted by stirring for 2 hours at room temperature. After completing reaction, the reaction solution was poured into 210 mL of 1.8% hydrochloric acid, the resultant crystal was filtered, then, the resultant crystal was dried, the crystal after drying was added to 70 mL of toluene, and was hot-dissolved to hot-filtered at the temperature of 100° C. Subsequently, the filtrate obtained by filtration was cooled with ice, and the precipitated crystal was filtered, then, the resultant crystal was dried to obtain 13.6 g of 9-anthrylmethyl N-n-propylcarbamate (yield: 93%) represented by the above-described formula [14] as yellow crystal. Measurement results of $^1$H-NMR and melting point are shown as the follows:

$^1$H-NMR (400 MHz, CDCl$_3$) δ (ppm): 0.89 (3H, t, J=7.2 Hz, CH$_3$), 1.47 (2H, qt, J=7.2, 6.8 Hz, CH$_2$), 3.15 (2H, br, NCH$_2$), 4.71 (1H, br, NH), 6.11 (2H, s, OCH$_2$), 7.45-7.55 (4H, m, ArH), 8.00 (2H, d, J=8.4 Hz, ArH), 8.37 (2H, d, J=8.4 Hz, ArH), 8.46 (1H, s, ArH);

Melting point: 164-167° C.

Example 6

Synthesis of 9-anthrylmethyl N-cyclohexylcarbamate (First and Second Process)

To the solution dissolved 8.92 g of N,N'-carbonyldiimidazole (55 mmol; produced by Wako Pure Chemical Industries, Ltd.) into 40 mL of dimethylformamide (DMF), 10.4 g of 9-anthracenemethanol (50 mmol; produced by Wako Pure Chemical Industries, Ltd.) was added under cooling with ice, then, the solution was reacted by stirring for 1 hour at the same temperature. Subsequently, 6.94 g of monocyclohexylamine (70 mmol; produced by Wako Pure Chemical Industries, Ltd.) was added to this solution, and the solution was reacted by stirring for 2 hours at room temperature. After completing reaction, the reaction solution was poured into 110 mL of 3.5% hydrochloric acid, the resultant crystal was filtered, then, the resultant crystal was dried, the crystal after drying was added to 100 mL of toluene, and was hot-dissolved to hot-filtered at the temperature of 100° C. Subsequently, the filtrate obtained by filtration was cooled with ice, and the precipitated crystal was filtered, then, the resultant crystal was dried to obtain 15.4 g of 9-anthrylmethyl N-cyclohexylcarbamate (yield: 92%) represented by the above-described formula [15] as yellow crystal. Measurement results of $^1$H-NMR and melting point are shown as the follows:

$^1$H-NMR (400 MHz, CDCl$_3$) δ (ppm): 1.06-1.09 (4H, br, CH$_2$×2), 1.32-1.36 (2H, br, CH$_2$), 1.60-1.66 (2H, br, CH$_2$), 1.91-1.92 (2H, br, CH$_2$), 3.53 (1H, br, NCH), 4.59 (1H, br, NH), 6.12 (2H, s, OCH$_2$), 7.46-7.58 (4H, m, ArH), 8.01 (2H, d, J=8.4 Hz, ArH), 8.39 (2H, d, J=8.4 Hz, ArH), 8.48 (1H, s, ArH); Melting point: 203-205° C.

Example 7

Synthesis of 9-anthrylmethyl 1-imidazolylcarboxylate (First Process)

To the Solution dissolved 8.92 g of N,N'-carbonyldiimidazole (55 mmol; produced by Wako Pure Chemical Industries, Ltd.) into 40 mL of dimethylformamide (DMF), 10.4 g of 9-anthracenemethanol (50 mmol; produced by Wako Pure Chemical Industries, Ltd.) was added under cooling with ice, then, the solution was reacted by stirring for 1 hour at the same temperature. After completing reaction, the reaction solution was poured into 200 mL of water, the resultant crystal was filtered, then, the resultant crystal was suspended in 100 mL of toluene, and slurry-washed at 40° C. Subsequently, the slurry-washed crystal was filtered, then, the resultant crystal was dried to obtain 13.1 g of 9-anthrylmethyl 1-imidazolylcarboxylate (yield: 87%) represented by the above-described formula [17] as yellow crystal. Measurement results of $^1$H-NMR and melting point are shown as the follows:

$^1$H-NMR (400 MHz, CDCl$_3$) δ (ppm): 6.44 (2H, s, OCH$_2$), 6.98 (1H, s, ArH), 7.34 (1H, s, ArH), 7.50-7.64 (4H, m, ArH), 8.05-8.07 (3H, m, ArH), 8.37 (2H, d, J=8.0 Hz, ArH), 8.57 (1H, s, ArH);

Melting point: 150-151° C.

Example 8

Synthesis of 9-anthrylmethyl N,N-di-n-octylcarbamate (Second Process)

To the solution dissolved 3.9 g of 9-anthrylmethyl 1-imidazolylcarboxylate (12.9 mmol) obtained by the same method as Example 7 and 1.84 g of methyl iodide (12.9 mmol; produced by Wako Pure Chemical Industries, Ltd.) into 13 mL of dimethylformamide (DMF), 3.71 g of di-n-octylamine (15.4 mmol; produced by Wako Pure Chemical Industries, Ltd.) was added at room temperature, then, the solution was reacted by stirring for 3 hours at 40° C. After completing reaction, ethyl acetate and water were poured into the reaction solution, and filtered out insoluble matter, then, this mixed solution was extracted, and further after organic layer after extraction was washed with water, the organic layer was condensed. The resultant condensed residue was purified with column chromatography (Filler: Silica-Gel (Wako-gel C-300HG; produced by Wako Pure Chemical Industries, Ltd.), Developing solvent: heptane/ethyl acetate=19/1) to obtain 1.03 g of 9-anthrylmethyl N,N-di-n-octylcarbamate (yield: 17%) represented by the above-described formula [9] as yellowish oil. Measurement results of $^1$H-NMR are shown as the follows:

$^1$H-NMR (400 MHz, CDCl$_3$) δ (ppm): 0.85 (6H, t, J=7.2 Hz, CH$_3$×2), 1.11-1.53 (24H, br, CH$_2$), 2.48 (4H, t, J=7.2 Hz, NCH$_2$×2), 4.48 (2H, s, OCH$_2$), 7.41-7.49 (4H, m, ArH), 7.98 (2H, d, J=8.4 Hz, ArH), 8.38 (1H, s, ArH), 8.54 (2H, d, J=8.4 Hz, ArH).

Example 9

Synthesis of 9-anthrylmethyl 1-(4-hydroxypiperidine)carboxylate (Second Process)

The solution dissolved 6.05 g of 9-anthrylmethyl 1-imidazolylcarboxylate (20 mmol) obtained by the same method as Example 7 and 2.12 g of 4-hydroxypiperidine (21 mmol; produced by Wako Pure Chemical Industries, Ltd.) into 20 mL of dimethylformamide (DMF) was reacted by stirring for 4 hours at room temperature. After completing reaction, the reaction solution was poured into 100 mL of 3.5% hydrochloric acid, the resultant crystal was filtered, then, the resultant crystal was dried, and the crystal after drying was added to 100 mL of toluene, and was hot-dissolved to hot-filtered at the temperature of 100° C. Subsequently, the filtrate obtained by filtration was cooled with ice, and the resultant crystal was filtered, then, the resultant crystal was dried to obtain 5.95 g of 9-anthrylmethyl 1-(4-hydroxypiperidine)carboxylate (yield: 89%) represented by the above-described formula [16]. Measurement results of $^1$H-NMR and melting point are shown as the follows:

$^1$H-NMR (400 MHz, CDCl$_3$) δ (ppm): 1.33-1.86 (5H, br, CH$_2$×2, CHO), 2.87-3.12 (2H, br, CH$_2$), 3.70-3.95 (3H, br, NCH$_2$, OH), 6.14 (2H, s, OCH$_2$), 7.48-7.57 (4H, m, ArH), 8.01 (2H, d, J=8.4 Hz, ArH), 8.38 (2H, d, J=8.4 Hz, ArH), 8.49 (1H, s, ArH);

Melting point: 192-194° C.

Example 10

Synthesis of 10-(9-bromoanthrylmethyl)N,N-diethylcarbamate

The solution dissolved 3.07 g of 9-anthrylmethyl N,N-diethylcarbamate (10 mmol) obtained by the same method as Example 4, 1.95 g of N-bromosuccinimide (11 mmol; produced by Wako Pure Chemical Industries, Ltd.) and 0.3 g of 2,2'-azobis(4-methoxy-2,4-dimethylvaleronitrile) (1 mmol; produced by Wako Pure Chemical Industries, Ltd.) into 20 mL of dichloromethane was reacted by stirring for 2 hours at 40° C. After completing reaction, the reaction solution was cooled, and ethyl acetate was poured into the cooled solution, then, the solution was washed with the saturated aqueous solution of sodium bicarbonate and water, and organic layer after washing was condensed. 20 mL of methanol was poured into the resultant condensed residue, and after the resultant crystal was filtered, the resultant crystal was dried to obtain 2.4 g of 10-(9-bromoanthrylmethyl)N,N-diethylcarbamate (yield: 63%) represented by the above-described formula [8] as yellow crystal. Measurement results of $^1$H-NMR and melting point are shown as the follows:

$^1$H-NMR (400 MHz, CDCl$_3$) δ (ppm): 0.91 (3H, br, CH$_3$), 1.15 (3H, br, CH$_3$), 3.11 (2H, br, NCH$_2$), 3.33 (2H, br, NCH$_2$), 6.12 (2H, s, OCH$_2$), 7.58 (2H, dd, J=8.0, 6.8 Hz, ArH), 7.63 (2H, dd, J=8.4, 6.8 Hz, ArH), 8.44 (2H, d, J=8.0 Hz, ArH), 8.46 (2H, d, J=8.4 Hz, ArH);

Melting point: 118° C.

Synthetic Example 4

Synthesis of 2-(1-bromo-1-ethyl)anthraquinone

To the solution dissolved 15.0 g of 2-ethylanthraquinone (63 mmol; produced by Wako Pure Chemical Industries, Ltd.) into 100 mL of dichloroethane, 11.3 g of N-bromosuccinimide (NBS) (63.5 mmol; produced by Wako Pure Chemical Industries, Ltd.) and 1.0 g of 2,2'-azobis(isobutyronitrile) (AIBN) (6.1 mmol; produced by Wako Pure Chemical Industries, Ltd.) were added, then, the solution was reacted by stirring for 2 hours at 60° C. After completing reaction, the reaction solution was condensed, and 120 mL of methanol was poured into the condensed residue, and after the resultant crystal was filtered, the resultant crystal was dried to obtain 18.0 g of 2-(1-bromo-1-ethyl)anthraquinone (yield: 90%) as pale yellow crystal. Measurement results of $^1$H-NMR are shown as the follows:

$^1$H-NMR (400 MHz, CDCl$_3$) δ (ppm): 2.12 (3H, d, J=7.2 Hz, CH$_3$), 5.30 (1H, q, J=7.2 Hz, CH), 7.81-7.83 (2H, m, ArH), 7.87-7.89 (1H, m, ArH), 8.30-8.35 (4H, m, ArH)

Synthetic Example 5

Synthesis of 2-anthraquinonyl-1-ethylalcohol 18.0 g of 2-(1-bromo-1-ethyl)anthraquinone (57.1 mmol) obtained by Synthetic Example 4 was suspended in the mixed solvent of 90 mL of acetone and 90 mL of water, 10.8 g of silver nitrate (63.6 mmol; produced by Wako Pure Chemical Industries, Ltd.) was added to this suspended solution, then, the solution was reacted by stirring for 1 hour at 40° C. After completing reaction, the reaction solution was cooled to room temperature, and the cooled solution was filtered through Celite, then, the filtrate was extracted by adding ethyl acetate, and further after organic layer after extraction was washed with water, the organic layer was condensed. The resultant condensed residue was purified with column chromatography (Filler: Silica-Gel (Wako-Gel C-200; produced by Wako Pure Chemical Industries, Ltd.), Developing solvent: ethyl acetate/n-hexane=1/1) to obtain 10.8 g of 2-anthraquinonyl-1-ethylalcohol (yield: 75%) as pale yellow crystal. Measurement results of $^1$H-NMR are shown as the follows:

$^1$H-NMR (400 MHz, CDCl$_3$) δ (ppm): 1.58 (3H, d, J=6.4 Hz, CH$_3$), 2.03 (1H, d, J=4.0 Hz, OH), 5.07-5.13 (1H, dq, J=4.0 Hz, 6.4 Hz, CH), 7.77-7.82 (2H, m, ArH), 7.83-7.86 (1H, m, ArH), 8.29-8.34 (4H, m, ArH)

Example 11

Synthesis of 2-anthraquinonyl-1-ethyl piperidinecarboxylate (First and Second Process)

To the solution dissolved 12.1 g of N,N'-carbonyldiimidazole (75 mmol; produced by Wako Pure Chemical Industries, Ltd) into 50 mL of dehydrated dimethylformamide (dehydrated DMF), 15.8 g of 2-anthraquinonyl-1-ethylalcohol (62 mmol) obtained by the same method as Synthetic Example 5 was added, then, the solution was reacted by stirring for 1 hour at room temperature. After completing reaction, ice-water was poured into the reaction solution, and this mixed solution was extracted with toluene, and further after organic layer after extraction was washed with water, the organic layer was condensed. The resultant condensed residue was purified with column chromatography (Filler: Silica-gel (Wako-gel C-200; produced by Wako Pure Chemical Industries, Ltd.), Developing solvent: ethyl acetate/n-heptane=1/9) to obtain 12.3 g of 2-anthraquinonyl-1-ethyl 1-imidazolylcarboxylate (yield: 57%) as yellow crystal. Subsequently, to the solution dissolved the resultant crystal of 2-anthraquinonyl-1-ethyl 1-imidazolylcarboxylate into 50 mL of dehydrated dimethylformamide (dehydrated DMF), 4.2 g of piperidine (50 mmol) was added, then, the solution was reacted for 1 hour at room temperature. After completing reaction, ice-water was poured into the reaction solution, this mixed solution was extracted with toluene, and further, organic layer after extraction was washed with water, the organic layer was condensed. The resultant condensed residue was purified with column chromatography (Filler: Silica-Gel (Wako-Gel C-200; produced by Wako Pure Chemical Industries, Ltd.), Developing solvent: ethyl acetate/n-heptane=1/9) to obtain 9.8 g of 2-anthraquinonyl-1-ethyl piperidinecarboxylate (yield: 43%) represented by the above-described formula [12] as yellow crystal. Measurement results of $^1$H-NMR and melting point are shown as the follows:

$^1$H-NMR (400 MHz, CDCl$_3$) δ (ppm): 1.59-1.61 (6H, m, 3×CH$_2$), 1.60 (3H, s, CH$_3$), 3.42-3.53 (4H, br, 2×NCH$_2$), 5.62 (1H, d, J=6.8 Hz, OCH), 7.73-7.81 (3H, m, ArH), 8.27-8.31 (4H, m, ArH);

Melting point: 107-113° C.

Example 12

Measurement Test of Ultraviolet-Visible Absorption Spectra

Acetonitrile solutions (about 5×10$^{-5}$ mol/L) of the compound obtained by Example 1 to 11 were prepared respectively, and were injected into quartz cell TOS-UV-10 (1 cm×1 cm×4 cm; manufactured by Toshinriko Co.), then, ultraviolet-visible absorption spectra were measured by using spectrophotometer UV-2550 (manufactured by Shimadzu Corp). Maximum absorption wavelength (nm) and molar absorption coefficient (c) in the maximum absorption wavelength, and molar absorption coefficient (ε) in 365 nm (i ray) and 405 nm (h ray) of these compounds are shown in Table 1.

TABLE 1

| Compound of the Present Invention | Maximum Absorption Wavelength (nm) (Molar Absorption Coefficient (ε)) | Maximum Absorption Wavelength (nm) in 300 nm or more of Wavelength (Molar Absorption Coefficient (ε)) | Molar Absorption Coefficent (ε) | |
|---|---|---|---|---|
| | | | 365 nm | 405 nm |
| Compound of Example 1 | 249 (57035) | 365 (8631) | 8631 | 34 |
| Compound of Example 2 | 255 (55869) | 325 (5575) | 275 | 80 |
| Compound of Example 3 | 241 (60303) | 341 (42863) | 407 | 0 |
| Compound of Example 4 | 250 (51324) | 365 (8846) | 8846 | 35 |
| Compound of Example 5 | 243 (38968) | 364 (10290) | 10163 | 30 |
| Compound of Example 6 | 251 (47254) | 364 (8941) | 8867 | 46 |
| Compound of Example 7 | 242 (62985) | 366 (9597) | 9458 | 76 |
| Compound of Example 8 | 253 (60126) | 366 (6253) | 5926 | 93 |
| Compound of Example 9 | 247 (59956) | 364 (9607) | 9558 | 7 |
| Compound of Example 10 | 248 (88080) | 375 (13323) | 5406 | 1940 |
| Compound of Example 11 | 254 (60974) | 325 (5685) | 357 | 126 |

Example 13

Measurement Test of Reactivity for Light (Active Energy Ray)

1 mg of the compound obtained by Example 1 to 4 was placed to quartz tube respectively, and was dissolved into 500 μL of acetonitrile. Subsequently, this solution was subjected to light (active energy rays) irradiation by 100 W high-pressure mercury lamp (HL-100 type; manufactured by Fuji-Glass Co.) for 10 minutes in 3 cm of measurement distance. Appropriate amounts of each solutions before and after irradiated with light (active energy rays) were spotted onto the TLC-plate (manufactured by Merck Co.), subsequently, ninhydrin spray (manufactured by Wako Pure Chemical Industries, Ltd.) was sprayed, and was heated by heat-gun for 30 seconds, and it was confirmed that whether ninhydrin reaction was occurred or not, that is, base (amine) can be released or not. Measurement results are shown in Table 2.

TABLE 2

| Compound of the Present Invention | Ninhydrin Reaction | |
|---|---|---|
| | Before Exposure | After Exposure |
| Compound of Example 1 | Negative | Positive |
| Compound of Example 2 | Negative | Positive |
| Compound of Example 3 | Negative | Positive |
| Compound of Example 4 | Negative | Positive |

Example 14

Measurement Test of Degradability of Light (Active Energy Rays)

The compounds obtained by Example 1 to 4 were weighed by 1.0 mg each by using electronic weighing instrument in NMR tube manufactured by quartz respectively, and were dissolved by adding 0.5 mL of deuterated acetonitrile. To this sample, all wavelength light (active energy ray) of high-pressure mercury lamp (SPOT CURE SP-III 250UA, type number: USH-255BY; manufactured by USHIO Inc.) was irradiated through filter-1, in which wavelength light less than 350 nm cannot be transmitted, by 100 J/cm$^2$ (i ray conversion: Ultraviolet intensity meter; UIT-150, photoreceiver: UVD-S365; manufactured by USHIO Inc.) before passing through filter, and 18.2 J/cm$^2$ (i ray conversion: Ultraviolet intensity meter; UIT-150, photoreceiver: UVD-S365; manufactured by USHIO Inc.) after passing through filter, and by comparing NMR spectra before and after irradiation, degradability for light (active energy ray) having wavelength range of 365 nm (i ray) or more was evaluated. Transmission curve of filter 1 was shown in FIG. 1, and evaluation results were shown in Table 3.

TABLE 3

| Compound of the Present Invention | Sensitivity of i Ray | |
|---|---|---|
| | 20 J/cm$^2$ | 100 J/cm$^2$ |
| Compound of Example 1 | ○ | ⊚ |
| Compound of Example 2 | ○ | ⊚ |
| Compound of Example 3 | ○ | ○ |
| Compound of Example 4 | ⊚ | ⊚ |

⊚: Photolysis of 50% or more of the compound occurs when irradiated.
○: Photolysis of less than 50% of the compound occurs when irradiated.

Example 15

Measurement test of Thermal Stability

TG-DTA measurement was carried out by using DTG-60 (manufactured by Shimadzu Corp.) in case of the compound obtained in Example 1 to 4, and TG-DTA 2000SA (manufactured by BRUKER AXS GmbH.) in case of the compound obtained in Example 5 to 11, in condition of 10° C./min of rate of temperature increase from 30° C. to 600° C., and the temperature (hereinafter, may be abbreviated as temperature of 5% weight loss), at which 5% weight loss from the initial weight by heating the compound of the present invention was occurred, was calculated, thereby heat resistance was evaluated. Evaluation results were shown in Table 4.

TABLE 4

| Compound of the Present Invention | Temperature of 5% Weight Loss |
|---|---|
| Compound of Example 1 | 250.4° C. |
| Compound of Example 2 | 254.5° C. |
| Compound of Example 3 | 244.0° C. |
| Compound of Example 4 | 240.6° C. |
| Compound of Example 5 | 239.1° C. |
| Compound of Example 6 | 251.1° C. |
| Compound of Example 7 | 135.3° C. |
| Compound of Example 8 | 236.9° C. |
| Compound of Example 9 | 207.4° C. |
| Compound of Example 10 | 215.8° C. |
| Compound of Example 11 | 285.7° C. |

Example 16

Hardening Test by Poly(Glycidyl Methacrylate)

1 mL solution of propyleneglycol monomethylether acetate (PGMEA) containing 0.2 g of poly(glycidyl methacrylate) and 20 wt % of the compound obtained by any of Example 1 to 11 based on 0.2 g of poly(glycidyl methacrylate) was spin-coated onto silicon wafer, and was heated for 1 minute at 100° C., and 1.5 µm of coated film was prepared. This coated film was irradiated for predetermined time by using the 2 kinds of instrument of ultraviolet irradiation source having specified exposure intensity, that is, combination of UIS-5011DUB4 (manufactured by USHIO Inc,) and LC-8 (manufactured by Hamamatsu Photonics K.K.) or combination of UIS-5011DUB4 (manufactured by USHIO Inc,) and SP-9 (manufactured by USHIO Inc,), or combination of UIS-5011DUB4 (manufactured by USHIO Inc,) and REX-250 (manufactured by Asahi Spectra Co., Ltd.), and each bases were generated from the compounds of Example 1 to 11, and in case of the coated film of the compound of Example 1 to 6 and Example 8 to 11, the coated film was hardened by heating for 2 hours at 120° C., and in case of the coated film by using the compound of Example 7, the coated film was hardened by heating for 10 minutes at 120° C. Further, this coated film was developed by immersing into acetone for 30 seconds, then, thickness of film was measured, and rate of film thickness before development and after development was measured as residual film rate. Exposure intensity in the specified wavelength of each instruments of optical source was shown in Table 5, and measurement results of residual film rate for irradiating ultraviolet ray per predetermined times were shown in FIGS. 2 to 12.

TABLE 5

| | UIS-5011DUB4 | LC-8 |
|---|---|---|
| 254 nm | 18.9 mW/cm$^2$ | 14.7 mW/cm$^2$ |
| 365 nm | 1.9 mW/cm$^2$ | 26.7 mW/cm$^2$ |
| 405 nm | 3.8 mW/cm$^2$ | 26.3 mW/cm$^2$ |

| | SP-9 | REX-250 |
|---|---|---|
| 254 nm | 18.9 mW/cm$^2$ | 1.24 mW/cm$^2$ |
| 365 nm | 25.1 mW/cm$^2$ | 25.6 mW/cm$^2$ |
| 405 nm | 26.3 mW/cm$^2$ | 40.8 mW/cm$^2$ |

From the results of Example 12 to 14, it is understood that the compounds of the present invention have photosensitive range in 200 nm or longer wavelength, and also high sensitivity for 300 nm or longer wavelength light (active energy rays). In addition, from showing comparatively large value of molar absorption coefficient in maximum absorption wavelength, it is clear that the base can be generated by even light (active energy rays) having weak exposure strength, such as the case that UIS-5011DUB4 was used in Example 16. Further, from the results of Table 4 obtained by Example 15, it is clear that, among the compound on the present invention, the compound which can generate the aliphatic amine as base is one in which temperature of 5% weight loss is higher than 200° C., and this is comparatively stable for heat. Therefore, for example, when the compound which can generate the aliphatic amine as the base, among the compound of the present invention, was used as the photobase generator, it is hard to decompose even in the heating process such as baking process in forming the coated film, thus, when heat resistance of the compound and the like are needed, it is understood that the compound which can generate the aliphatic amine as the base is more desirable than the compound which can generate the aromatic amine as the base. On the other hand, for example, like the compound obtained by Example 7, the compound which can generate the aromatic amine as the base is insufficient for heat resistance from the results of Table 4 obtained by Example 15, but, as is obvious from the results obtained by Example 16, for example, when this compound is used for hardening of the epoxy resin such as poly(glycidyl methacrylate), the compound is very sensitive, and can be excellently hardened in a short time, thus, when the compound is used as the photobase generator, in case that heat resistance of the photobase generator gives no problem, there may be case that the compound which can generate the aromatic amine as the base is desirable. In addition, the compound which has problem for heat resistance, in other words, it is suggested that the compound can generate the base due to decomposing when heated, thus, it may be referred as suitable compound for the heat-base generator. Furthermore, as is obvious from the results of FIGS. 2 to 12 obtained by Example 16, in the compounds of the present invention, among the compound which can generate the aliphatic amine as the base, for example, it is understood that comparing with the compound (the compound of Example 8) which can generate the organic amine (base) having comparatively long carbon atoms such as dioctylamine, for example, the compound (the compounds of Example 1 to 6 and 9 to 11) which can generate the organic amine (base) having comparatively short carbon atoms such as diethylamine, n-propylamine, cyclohexylamine, piperidine, 4-hydroxypiperidine can rather harden the coated film of the epoxy resin and the like in a short time. That is, for example, judging from these results that the organic amine having comparatively long carbon atoms such as dioctylamine is bulky, thus, it is difficult to occur nucleophilic reaction to an epoxy group, therefore, it is difficult to progress hardening by the epoxy group, on the other hand, the organic amine (base) having comparatively short carbon atoms such as diethylamine, n-propylamine, cyclohexylamine, piperidine, 4-hydroxypiperidine have high nucleophilicity, so, it is expected to progress comparatively excellently the hardening reaction by the epoxy group. From this situation, it is understood that, like the hardening of the epoxy group, as for the coated film which progresses the hardening by the results that the organic amine (base) generated from the compound bring about the nucleophilic reaction, among the compounds which generate the aliphatic amine as the base, the compound which can generate the organic amine (base) having comparatively short carbon atoms such as 1 to 6 carbon atoms is preferable. As mentioned above, it is understood that the compounds of the present invention generate sufficient base for hardening resin, and also, have high sensitivity for 254 nm wavelength light (active energy rays) which is irradiated to the conventional photobase generator, as well as have excellent sensitivity for longer wavelength light (active energy rays) such as 365 nm, 405 nm, can harden the resin by generating the base efficiently with longer wavelength light (active energy rays) according to the compound.

From these results, it is suggested that the reason why the compound of the present invention can efficiently generate a base by irradiated with longer wavelength light (active energy rays) than the conventional wavelength (active energy rays) is due to that, in its structure, it has the specified tri- or tetra-cyclic aromatic hydrocarbon group showing sufficient photo sensitivity even for longer wavelength light (active energy rays), and has urethane structure which can efficiently liberate the base (amine). In addition, from these results, the compound of the present invention was found to be useful, for example, as the photobase generator for hardening the resin.

INDUSTRIAL APPLICABILITY

The compound of the present invention can generate a base by irradiated with longer wavelength light (active energy rays) comparing with the light (active energy rays) to which conventional photobase generator is exposed, therefore, the compound is useful as the photobase generator for hardening resin, and the photo-hardening resin material using the photobase generator.

What is claimed is:

1. A compound represented by the formula [7]:

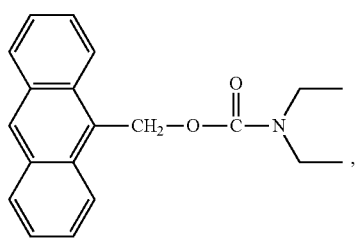

[7]

a compound represented by the formula [8]:

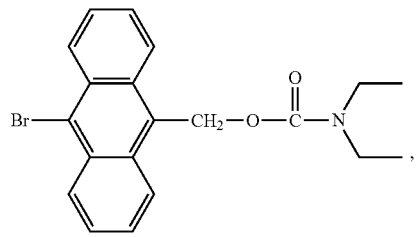

[8]

a compound represented by the formula [14]:

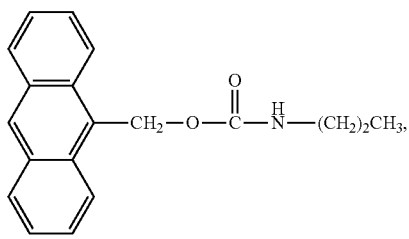

[14]

a compound represented by the formula [16]:

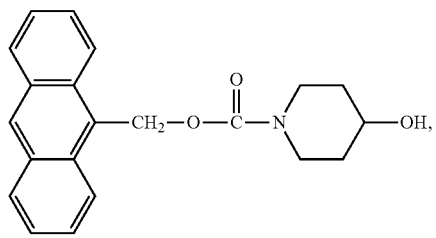

[16]

or a compound represented by the general formula [1]

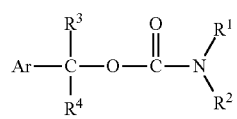

[1]

wherein Ar represents
an anthraquinonyl group represented by the general formula [II]:

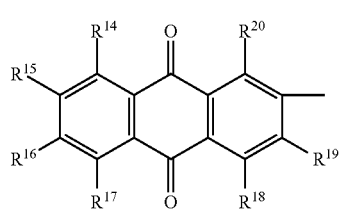

[II]

wherein $R^{14}$ to $R^{20}$ each represents a hydrogen atom, and $R^1$ and $R^2$ each independently represents a hydrogen atom, or a linear, branched or cyclic alkyl group having 1 to 10 carbon atoms, or represent groups which can form an alicyclic ring containing nitrogen atom(s) or an aromatic ring containing nitrogen atom(s) together with the nitrogen atom that is bound to R1 and R2 in the general formula [1], and wherein the rings have 3 to 8 carbon atoms which may have substituent(s) selected from the group consisting of a methyl group, an ethyl group, a hydroxyl group, a mercapto group, a cyano group, a nitro group and a halogen atom, and $R^3$ and $R^4$ each independently represents a hydrogen atom or a linear, branched or cyclic alkyl group having 1 to 10 carbon atoms.

2. The compound according to claim 1, wherein $R^1$ and $R^2$ in the general formula [1] are both linear alkyl groups having 1 to 8 carbon atoms.

3. The compound according to claim 1, wherein $R^1$ and $R^2$ in the general formula [1] are both linear alkyl groups having 1 to 6 carbon atoms.

4. The compound according to claim 1, wherein $R^1$ and $R^2$ in the general formula [1] form an alicyclic ring containing nitrogen atom(s) together with the nitrogen atom that is bound to $R^1$ and $R^2$ in the general formula [1], and wherein the ring has 4 to 7 carbon atoms and has no substituent.

5. The compound according to claim 1, wherein $R^1$ in the general formula [1] is a hydrogen atom, $R^2$ is a linear or cyclic alkyl group having 3 to 8 carbon atoms.

6. The compound according to claim 1, wherein $R^1$ and $R^2$ in the general formula [1] form an alicyclic ring containing nitrogen atom(s) together with the nitrogen atom that is bound to R1 and R2 in the general formula [1], and wherein the ring has 5 carbon atoms which has substituent(s) selected from the group consisting of a methyl group, an ethyl group, a hydroxyl group, a mercapto group, a cyano group, a nitro group and a halogen atom.

7. The compound according to claim 1, wherein $R^1$ and $R^2$ in the general formula [1] form an aromatic ring containing nitrogen atom(s) together with the nitrogen atom that is bound to R1 and R2 in the general formula [1], and wherein the ring has 3 to 4 carbon atoms and has no substituent.

8. The compound according to claim 1, wherein $R^3$ and $R^4$ in the general formula [1] are both hydrogen atoms.

9. The compound according to claim 1, wherein $R^3$ is a hydrogen atom, $R^4$ is a linear alkyl group having 1 to 3 carbon atoms in the general formula [1].

10. The compound according to claim 1, wherein Ar in the general formula [1] is an anthraquinonyl group represented by the general formula [II']:

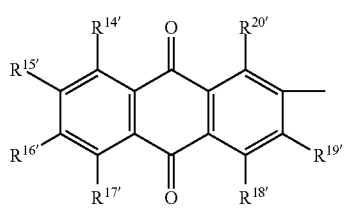

wherein $R^{14\prime}$ to $R^{20\prime}$ represent a hydrogen atom.

11. The compound according to claim 1, wherein the compound is one represented by the formula [7]:

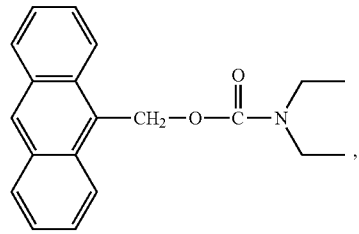

one represented by the formula [8]:

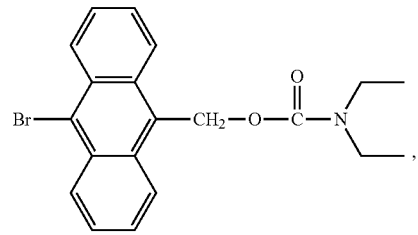

one represented by the formula [11]:

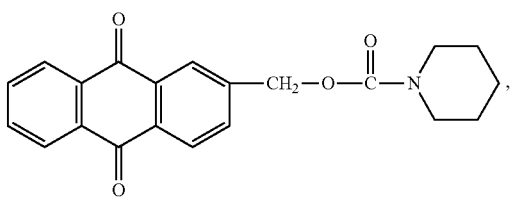

one represented by the formula [12]:

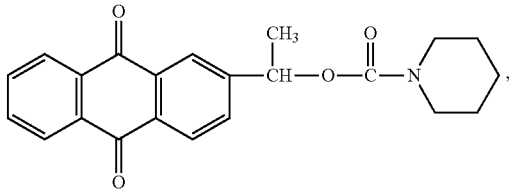

one represented by the formula [14]:

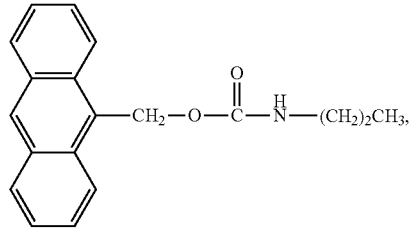

or one represented by the formula [16]:

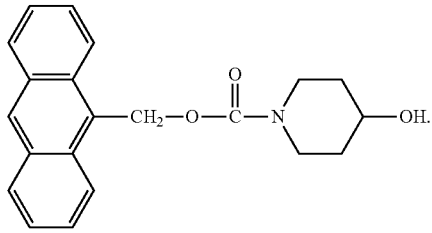

12. A photobase generator, comprising:

a compound represented by the formula [7]:

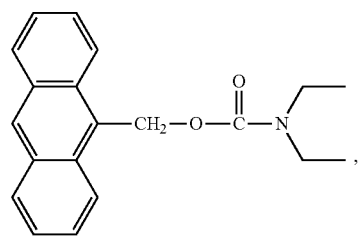

a compound represented by the formula [8]:

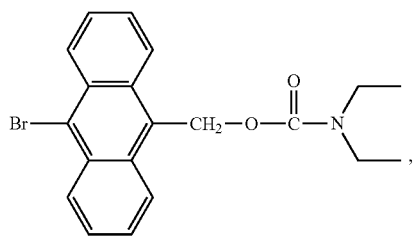

a compound represented by the formula [14]:

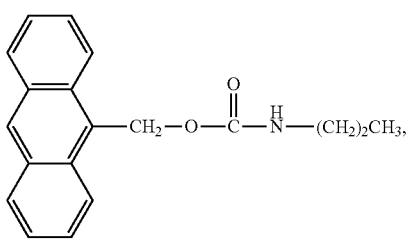

a compound represented by the formula [16]:

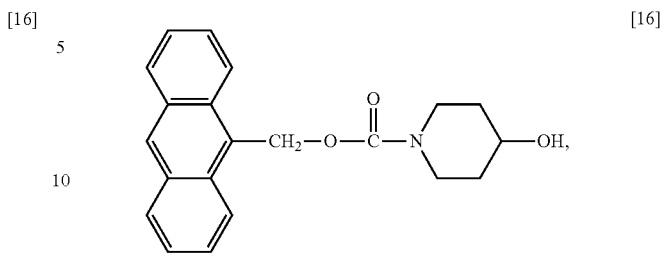

or
a compound represented by the general formula [1]

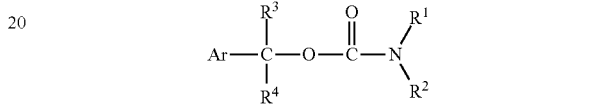

wherein Ar represents an anthraquinonyl group represented by the general formula [II]:

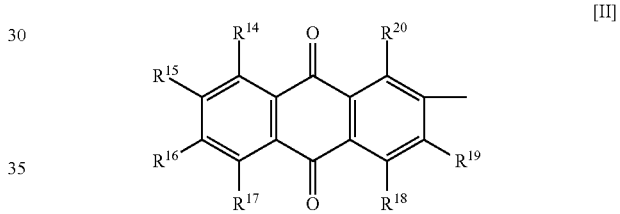

wherein $R^{14}$ to $R^{20}$ each represents a hydrogen atom, and $R^1$ and $R^2$ each independently represents a hydrogen atom, or a linear, branched or cyclic alkyl group having 1 to 10 carbon atoms, or represent groups which can form an alicyclic ring containing nitrogen atom(s) or an aromatic ring containing nitrogen atom(s) together with the nitrogen atom that is bound to R1 and R2 in the general formula [1], and wherein the rings have 3 to 8 carbon atoms which may have substituent(s) selected from the group consisting of a methyl group, an ethyl group, a hydroxyl group, a mercapto group, a cyano group, a nitro group and a halogen atom, and $R^3$ and $R^4$ independently represents a hydrogen atom or a linear, branched or cyclic alkyl group having 1 to 10 carbon atoms.

13. The photobase generator according to claim 12, which generates the base when irradiated with 200 nm to 500 nm wavelength light.

14. A base generating method characterized in that the compound according to claim 1 is irradiated with light.

15. The photobase generator according to claim 12, wherein $R^1$ and $R^2$ in the general formula [1] are both linear alkyl groups having 1 to 8 carbon atoms.

16. The photobase generator according to claim 12, wherein $R^1$ and $R^2$ in the general formula [1] are both linear alkyl groups having 1 to 6 carbon atoms.

17. The photobase generator according to claim 12, wherein $R^1$ and $R^2$ in the general formula [1] form an alicyclic ring containing nitrogen atom(s) together with the nitrogen atom that is bound to R1 and R2 in the general formula [1], and wherein the ring has 4 to 7 carbon atoms and has no substituent.

18. The photobase generator according to claim 12, wherein R¹ in the general formula [1] is a hydrogen atom, and R² is a linear or cyclic alkyl group having 3 to 8 carbon atoms.

19. The photobase generator according to claim 12, wherein R¹ and R² in the general formula [1] form an alicyclic ring containing nitrogen atom(s) together with the nitrogen atom that is bound to R1 and R2 in the general formula [1], and wherein the ring has 5 carbon atoms and has a substituent(s) selected from the group consisting of a methyl group, an ethyl group, a hydroxyl group, a mercapto group, a cyano group, a nitro group and a halogen atom.

20. The photobase generator according to claim 12, wherein R¹ and R² in the general formula [1] form an aromatic ring containing nitrogen atom(s) together with the nitrogen atom that is bound to R1 and R2 in the general formula [1], and wherein the ring has 3 to 4 carbon atoms and has no substituent.

21. The photobase generator according to claim 12, wherein R³ and R⁴ in the general formula [1] are both hydrogen atoms.

22. The photobase generator according to claim 12, wherein R³ is a hydrogen atom, R⁴ is a linear alkyl group having 1 to 3 carbon atoms in the general formula [1].

23. The photobase generator according to claim 12, wherein Ar in the general formula [1] is an anthraquinonyl group represented by the general formula [II']:

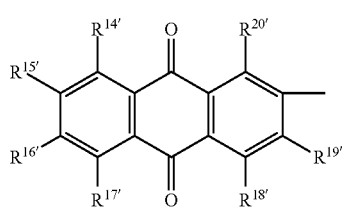

(wherein, R¹⁴' to R²⁰' represent a hydrogen atom).

24. The photobase generator according to claim 12, wherein the compound is one represented by the formula [7]:

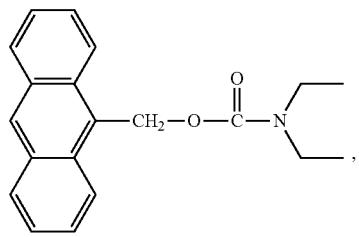

one represented by the formula [8]:

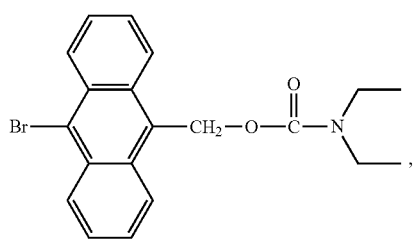

one represented by the formula [11]:

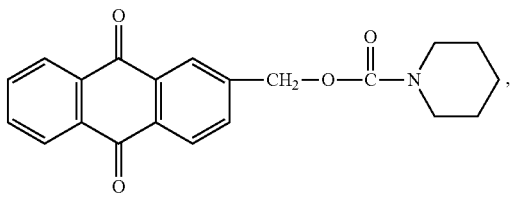

one represented by the formula [12]:

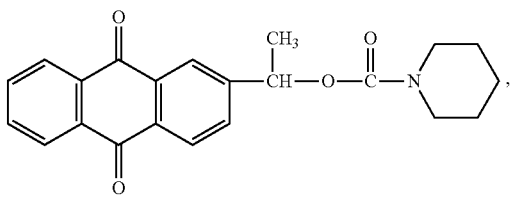

one represented by the formula [14]:

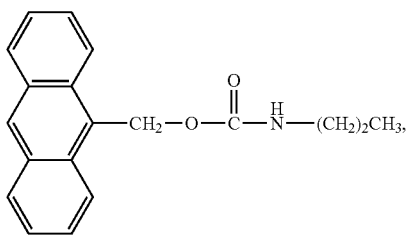

or, one represented by the formula [16]:

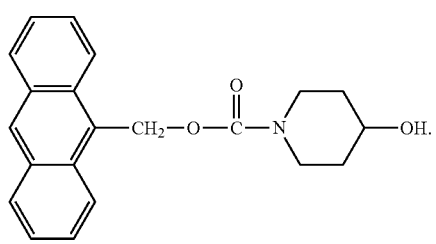

25. The photobase generator according to claim 12, wherein the compound is one represented by the formula [7]:

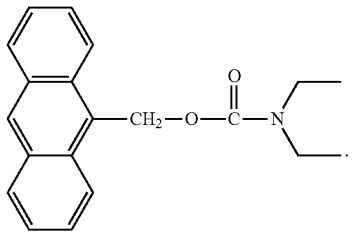

26. The photobase generator according to claim 12, wherein the compound is 2-anthraquinonyl-1-ethyl 1-imidazolylcarboxylate.

27. The compound according to claim 1, wherein the compound is one represented by the formula [7]:

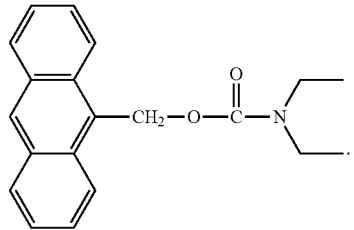

28. The compound according to claim 1, wherein the compound is 2-anthraquinonyl-1-ethyl 1-imidazolylcarboxylate.

* * * * *